(12) United States Patent
Zhang et al.

(10) Patent No.: US 11,325,987 B2
(45) Date of Patent: May 10, 2022

(54) SOLID STATE NANOPORES AIDED BY MACHINE LEARNING FOR IDENTIFICATION AND QUANTIFICATION OF HEPARINS AND GLYCOSAMINOGLYCANS

(71) Applicant: ARIZONA BOARD OF REGENTS ON BEHALF OF ARIZONA STATE UNIVERSITY, Scottsdale, AZ (US)

(72) Inventors: Peiming Zhang, Gilbert, AZ (US); Xu Wang, Tempe, AZ (US); Jong One Im, Tempe, AZ (US); Stuart Lindsay, Phoenix, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 851 days.

(21) Appl. No.: 16/155,972

(22) Filed: Oct. 10, 2018

(65) Prior Publication Data

US 2019/0256616 A1    Aug. 22, 2019

Related U.S. Application Data

(60) Provisional application No. 62/571,077, filed on Oct. 11, 2017.

(51) Int. Cl.
*G01N 33/48* (2006.01)
*G01N 33/50* (2006.01)
(Continued)

(52) U.S. Cl.
CPC ...... *C08B 37/0075* (2013.01); *C08B 37/0069* (2013.01); *G06N 3/08* (2013.01);
(Continued)

(58) Field of Classification Search
CPC ............ C08B 37/0075; C08B 37/0069; G06N 20/10; G06N 3/08; G16B 40/20; G16B 40/10
See application file for complete search history.

(56) References Cited

U.S. PATENT DOCUMENTS 7,968,082 B1    6/2011    Shriver et al.
8,435,795 B2    5/2013    Beccati et al.
(Continued)

FOREIGN PATENT DOCUMENTS

WO    2006124089 A1    11/2006
WO    2007139849 A2    12/2007
(Continued)

OTHER PUBLICATIONS

Shasha, C , et al., "Nanopore-based conformational analysis of a viral RNA drug target", ACS Nano 8(6), 6425-6430 (2014).
(Continued)

*Primary Examiner* — Russell S Negin
(74) *Attorney, Agent, or Firm* — Viksnins Harris Padys Malen LLP

(57) ABSTRACT

The present disclosure provides a method for identifying and quantifying sulfated glycosaminoglycans, including for example heparin, by passing a sample through nanopores. The glycosaminoglycans sample is measured in microliter quantities, at nanomolar concentrations with detection of impurities below 0.5%, and a dynamic range over five decades of magnitude with a trained machine learning algorithm.

6 Claims, 12 Drawing Sheets

(51) Int. Cl.
  *C08B 37/00* (2006.01)
  *G06N 20/10* (2019.01)
  *G16B 40/20* (2019.01)
  *G06N 3/08* (2006.01)
  *G16B 40/10* (2019.01)

(52) U.S. Cl.
  CPC .............. *G06N 20/10* (2019.01); *G16B 40/10* (2019.02); *G16B 40/20* (2019.02)

(56) References Cited

U.S. PATENT DOCUMENTS

| | | |
|---|---|---|
| 8,628,649 B2 | 1/2014 | Lindsay et al. |
| 8,685,894 B2 | 4/2014 | Chaput et al. |
| 8,961,757 B2 | 2/2015 | Nuckolls et al. |
| 8,968,540 B2 | 3/2015 | Reinhart et al. |
| 8,980,073 B2 | 3/2015 | Pourmand et al. |
| 9,140,682 B2 | 9/2015 | Lindsay et al. |
| 9,395,352 B2 | 7/2016 | Lindsay et al. |
| 9,593,372 B2 | 3/2017 | Lindsay et al. |
| 9,766,248 B2 | 9/2017 | Lindsay et al. |
| 9,810,681 B2 | 11/2017 | Lindsay et al. |
| 9,952,198 B2 | 4/2018 | Lindsay et al. |
| 9,981,997 B2 | 5/2018 | Zhang et al. |
| 10,139,417 B2 | 11/2018 | Lindsay et al. |
| 10,145,846 B2 | 12/2018 | Lindsay et al. |
| 10,267,785 B2 | 4/2019 | Lindsay et al. |
| 10,330,632 B2 | 6/2019 | Lindsay et al. |
| 10,336,713 B2 | 7/2019 | Zhang et al. |
| 10,379,102 B2 | 8/2019 | Lindsay et al. |
| 10,422,787 B2 | 9/2019 | Lindsay et al. |
| 10,442,771 B2 | 10/2019 | Lindsay et al. |
| 10,444,220 B2 | 10/2019 | Lindsay et al. |
| 2006/0073489 A1 | 4/2006 | Li et al. |
| 2009/0018028 A1 | 1/2009 | Lindsay et al. |
| 2011/0048946 A1 | 3/2011 | Desai et al. |
| 2013/0302901 A1 | 11/2013 | Lindsay et al. |
| 2015/0144506 A1 | 5/2015 | Lindsay et al. |
| 2016/0108002 A1 | 4/2016 | Zhang et al. |
| 2017/0343558 A1 | 11/2017 | Lindsay et al. |
| 2019/0195856 A1 | 6/2019 | Zhang et al. |
| 2019/0195884 A1 | 6/2019 | Lindsay et al. |
| 2019/0242885 A1 | 8/2019 | Lindsay et al. |
| 2019/0250127 A1 | 8/2019 | Zhang et al. |
| 2019/0317040 A1 | 10/2019 | Lindsay et al. |
| 2019/0353635 A1 | 11/2019 | Lindsay et al. |
| 2020/0033320 A1 | 1/2020 | Lindsay et al. |

FOREIGN PATENT DOCUMENTS

| | | |
|---|---|---|
| WO | 2008124706 A2 | 10/2008 |
| WO | 2008124706 A9 | 5/2009 |
| WO | 2009117517 A2 | 9/2009 |
| WO | 2009117522 A2 | 9/2009 |
| WO | 2010042514 A1 | 4/2010 |
| WO | 2011097171 A1 | 8/2011 |
| WO | 2013116509 A1 | 8/2013 |
| WO | 2013151756 A1 | 10/2013 |
| WO | 2013180819 A1 | 12/2013 |
| WO | 2013151756 A9 | 3/2014 |
| WO | 2014138253 A1 | 9/2014 |
| WO | 2014190299 A2 | 11/2014 |
| WO | 2014194246 A1 | 12/2014 |
| WO | 2015065985 A1 | 5/2015 |
| WO | 2015131073 A1 | 9/2015 |
| WO | 2015161119 A1 | 10/2015 |
| WO | 2018039129 A1 | 3/2018 |
| WO | 2018064078 A1 | 4/2018 |

OTHER PUBLICATIONS

Sonnefeld, J , "Determination of surface charge density parameters of silicon nitride", Colloids and Surfaces A: Physicochemical and Engineering Aspects 108(1), 27-31 (1996).

Staples, G , et al., "A chip-based amide-HILIC LC/MS platform for glycosaminoglycan glycomics profiling", Proteomics 9, 686-695 (2009).

Sun, X , et al., "Capillary Electrophoresis-Mass Spectrometry for the Analysis of Heparin Oligosaccharides and Low Molecular Weight Heparin", Analytical Chemistry 88(3), 1937-1943 (2016).

Takemasa, M , et al., "Glycan Analysis Using a Solid State Nanopore", Nanopores for Bioanalytical Applications: Proceedings of the International Conference, 89-92 (2012).

Trehy, M , et al., "Analysis of heparin sodium by SAX/HPLC for contaminants and impurities", Journal of Pharmaceutical and Biomedical Analysis 49(3), 670-673 (2009).

Tremblay, J , "Making Heparing Safe", Chemical and Engineering News 94(40), 30-34 (2016).

Van Den Hoogen, B , et al., "A microtiter plate assay for the determination of uronic acids", Analytical Biochemistry 257(2), 107-111 (1998).

Vercoutere, W , et al., "Rapid discrimination among individual DNA hairpin molecules at single-nucleotide resolution using an ion channel", Nature Biotechnology 19, 248-252 (2001).

Waduge, P , et al., "Nanopore-Based Measurements of Protein Size, Fluctuations, and Conformational Changes", ACS Nano 11(6), 5706-5716 (2017).

Wang, W , et al., "Supercharged Fluorescent Protein as a Versatile Probe for the Detection of Glycosaminoglycans in Vitro and in Vivo", Analytical Chemistry 87(18), 9302-9307 (2015).

Wanunu, M , et al., "Electrostatic focusing of unlabelled DNA into nanoscale pores using a salt gradient", Nature Nanotechnology 5, 160-165 (2010).

Wanunu, M , et al., "Rapid electronic detection of probe-specific microRNAs using thin nanopore sensors", Nature Nanotechnology 5, 807-814 (2010).

Winters-Hilt, S , et al., "Nanopore Cheminformatics", DNA and Cell Biology 23(10), 675-683 (2004).

Zahid, O , et al., "Sequence-Specific Recognition of MicroRNAs and Other Short Nucleic Acids with Solid-State Nanopores", Nano letters 16(3), 2033-2039 (2016).

Zaia, J , "On-line Separations Combined with MS for Analysis of Glycosaminoglycans", Mass Spectrometry Reviews 28, 254-272 (2009).

U.S. Appl. No. 16/597,837, Lindsay et al, filed Oct. 9, 2019.

Afratis, N , et al., "Glycosaminoglycans: key players in cancer cell biology and treatment", The FEBS Journal 279, 1177-1197 (2012).

Albrecht, T , et al., "Deep learning for single-molecule science", Nanotechnology 28(423001), 11 pages (2017).

Bishop, J , et al., "Heparan sulphate proteoglycans fine-tune mammalian physiology", Nature 446, 1030-1037 (2007).

Boza, V, et al., "DeepNano: Deep recurrent neural networks for base calling in MinION nanopore reads", PLoS One 12(e0178751), 13 pages (2017).

Cajfinger, F , et al., "Low-molecular-weight heparins for cancer-associated thrombosis: Adherence to clinical practice guidelines and patient perception in Tropique, a 409-patient prospective observational study", Thrombosis Research 144, 85-92 (2016).

Chang, S , et al., "Chemical recognition and binding kinetics in a functionalized tunnel junction", Nanotechnology 23 (235101), 14 pages (2012).

Chaudhari, K , et al., "Antithrombotic drugs market", Nature Reviews Drug Discovery 13, 571-572 (2014).

Cosmi, B , et al., "Old and New Heparins", Thrombosis Research 129(3), 388-391 (2012).

Dantuluri, M , et al., "Capillary electrophoresis of sulfated molecules", Recent Res. Dev. Anal. Biochem. 3, 169-186 (2003).

Dekker, C , "Solid-state nanopores", Nature Nanotechnology 2, 209-215 (2007).

Ding, Y , et al., "A supercharged fluorescent protein based FRET sensing platform for detection of heparin contamination", Analytical Methods 9(38), 5593-5597 (2017).

Dong, Z , et al., "Discriminating Residue Substitutions in a Single Protein Molecule Using a Sub-nanopore", ACS Nano 11(6), 5440-5452 (2017).

(56) References Cited

OTHER PUBLICATIONS

Ellett, L., et al., "Glycosaminoglycan sulfation determines the biochemical properties of prion protein aggregates", Glycobiology 25(7), 745-755 (2015).
Engelberg, H., et al., "Plasma Heparin Levels in Normal Man", Circulation XXIII, 578-581 (1961).
Feng, Y., et al., "Nanopore-based fourth-generation DNA sequencing technology", Genomics, Proteomics & Bioinformatics 13(1), 4-16 (2015).
Fennouri, A, et al., "Single Molecule Detection of Glycosaminoglycan Hyaluronic Acid Oligosaccharides and Depolymerization Enzyme Activity Using a Protein Nanopore", ACS Nano 6(11), 9672-9678 (2012).
Garalde, D., et al., "Highly parallel direct RNA sequencing on an array of nanopores", bioRxiv, 21 pages (2016).
Garalde, D., et al., "Highly parallel direct RNA sequencing on an array of nanopores", Nature Methods 15(3), 201-206 (2018).
Guerrini, M., et al., "Orthogonal analytical approaches to detect potential contaminants in heparin", Proceedings of the National Academy of Sciences of the United States of America 106(40), 16956-16961 (2009).
Hasegawa, M., et al., "Alzheimer-like Changes in Microtubule-associated Protein Tau Induced by Sulfated Glycosaminoglycans", The Journal of Biological Chemistry 272(52), 33118-33124 (1997).
Henley, R., et al., "Electrophoretic Deformation of Individual Transfer RNA Molecules Reveals Their Identity", Nano Letters 16(1), 138-144 (2016).
Im, J., et al., "Electronic single-molecule identification of carbohydrate isomers by recognition tunnelling", Nature Communications 7(13868), 7 pages (2016).
Jethava, V., et al., "svm-theta", GitHub (2012), retrieved as is on May 8, 2019 <URL:https://github.com/vjethava/svm-theta>.
Kalita, M., et al., "A Nanosensor for Ultrasensitive Detection of Oversulfated Chondroitin Sulfate Contaminant in Heparin", Journal of the American Chemical Society 136(2), 554-557 (2014).
Kang, Y., et al., "Highly sensitive potentiometric strip test for detecting high charge density impurities in heparin", Analytical Chemistry 83(10), 3957-3962 (2011).
Karawdeniya, B., et al., "Surveying silicon nitride nanopores for glycomics and heparin quality assurance", Nature Communications 9(3278), 8 pages (2018).
Kareva, I., et al., "Normal Wound Healing and Tumor Angiogenesis as a Game of Competitive Inhibition", PLoS One 11(e0166655), 16 pages (2016).
Keire, D., et al., "Analysis of crude heparin by (1)H NMR, capillary electrophoresis, and strong-anion-exchange-HPLC for contamination by over sulfated chondroitin sulfate", Journal of Pharmaceutical and Biomedical Analysis 51(4), 921-926 (2010).
Keire, D., et al., "Assay of possible economically motivated additives or native impurities levels in heparin by 1H NMR, SAX-HPLC, and anticoagulation time approaches", Journal of Pharmaceutical and Biomedical Analysis 52(5), 656-664 (2010).
Kim, M., et al., "Characteristics of solid-state nanometre pores fabricated using a transmission electron microscope", Nanotechnology 18(205302), 5 pages (2007).

Lamari, F., et al., "Structure of Chondroitin Sulfate", Advances in Pharmacology 53, 33-48 (2006).
Lan, W., et al., "Voltage-Rectified Current and Fluid Flow in Conical Nanopores", Accounts of Chemical Research 49 (11), 2605-2613 (2016).
Lee, H., et al., "Dual Role of a Fluorescent Peptidyl Probe Based on Self-Assembly for the Detection of Heparin and for the Inhibition of the Heparin-Digestive Enzyme Reaction", ACS Applied Materials & Interfaces 10(3), 2282-2290 (2018).
Lee, C., et al., "Molecular Beacon-Based Fluorescent Assay for Specific Detection of Oversulfated Chondroitin Sulfate Contaminants in Heparin without Enzyme Treatment", Analytical Chemistry 87(10), 5031-5035 (2015).
Lee, S., et al., "Scientific considerations in the review and approval of generic enoxaparin in the United States", Nature Biotechnology 31(3), 220-226 (2013).
Lester, J., et al., "Reversible Electrochemical Sensor for Detection of High-Charge Density Polyanion Contaminants in Heparin", Analytical Chemistry 87(22), 11537-11543 (2015).
Lin, L., et al., "Analysis of heparin oligosaccharides by capillary electrophoresis-negative-ion electrospray ionization mass spectrometry", Analytical and Bioanalytical Chemistry 409(2), 411-420 (2017).
Mizumoto, S., et al., "Glycosaminoglycans are functional ligands for receptor for advanced glycation end-products in tumors", The FEBS Journal 280, 2462-2470 (2013).
Mourier, P., et al., "Analytical and statistical comparability of generic enoxaparins from the US market with the originator product", Journal of Pharmaceutical and Biomedical Analysis 115, 431-442 (2015).
Nemes, P, et al., "High-Throughput Differentiation of Heparin from Other Glycosaminoglycans by Pyrolysis Mass Spectrometry", Analytical Chemistry 85(15), 7405-7412 (2013).
Nishitsuji, K., et al., "Sulfated glycosaminoglycans in protein aggregation disease", Glycoconjugate Journal 34(4), 453-466 (2017).
Olczyk, P., et al., "Diverse Roles of Heparan Sulfate and Heparin in Wound Repair", BioMed Research International (2015)549417, 7 pages (2015).
Onishi, A., et al., "Heparin and anticoagulation", Frontiers in Bioscience 21, 1372-1392 (2016).
Piran, S., et al., "Management of recurrent venous thromboembolism in patients with cancer: A review", Thrombosis Research 164(1), S172-S177 (2018).
Rabenstein, D., et al., "Heparin and heparan sulfate: structure and function", Natural Product Reports 19, 312-331 (2002).
Rivas, F., et al., "Label-free analysis of physiological hyaluronan size distribution with a solid-state nanopore sensor", Nature Communications 9(1037), 9 pages (2018).
Sasisekharan, R., et al., "Heparin and heparan sulfate: biosynthesis, structure and function", Current Opinion in Chemical Biology 4(6), 626-631 (2000).
Sasisekharan, R, et al., "Roles of heparansulphate glycosaminoglycans in cancer", Nature Reviews Cancer 2, 521-528 (2002).
Schibel, A., et al., "Nanopore Membranes for Single-Molecule Detection and Characterization", The University of Utah Department of Chemistry, 11 slides (2007), retrieved online May 8, 2019 <URL:ion.chem.usu.edu/~tapaskar/nanoutah07/M-T2-2.ppt>.

SOLID STATE NANOPORES AIDED BY MACHINE LEARNING FOR IDENTIFICATION AND QUANTIFICATION OF HEPARINS AND GLYCOSAMINOGLYCANS

CROSS REFERENCE TO RELATED APPLICATIONS

This non-provisional application filed under 37 CFR § 1.53(b), claims the benefit under 35 USC § 119(e) of U.S. Provisional Application Ser. No. 62/571,077 filed on 11 Oct. 2017, which is incorporated by reference in entirety.

GOVERNMENT SUPPORT

This invention was made with government support under R21 GM118339 and U01 CA221235 awarded by the National Institutes of Health. The government has certain rights in the invention.

TECHNICAL FIELD

This invention is related to a means and method for identifying sulfated glycosaminoglycans in microliter quantities, at nanomolar concentrations with detection of impurities below 0.5% and a dynamic range over five decades of magnitude.

BACKGROUND

Heparins are a class of complex biomacromolecules, sulfated glycosaminoglycan (GAG) polysaccharides. Heparin, a highly sulfated glycosaminoglycan (GAG), is known for its anticoagulation activity, making it one of the most widely used blood thinners in medicine (Onishi, A., et al, (2016) *Front. Biosci.* 21, 1372-1392). Low molecular weight heparins (LMWHs) are the major type of heparin for antithrombotic use (Chaudhari, K., et al, (2014) *Nat. Rev. Drug Discov* 13, 571-572) and the first line choice for cancer-associated thrombosis (Cajfinger, F. et al. (2016) *Thromb. Res.* 144, 85-92; Piran, S. & Schulman, S. (2018) *Thromb. Res.* 164 (Suppl 1), S172-S177). Biologically, heparin plays regulatory roles in physiological and pathological processes such as cell growth and development, cancer progression, neurodegenerative diseases, normal wound healing, and tumor angiogenesis. Sulfated GAGs may also represent a class of promising biomaterials for tissue engineering, repair, and reconstruction.

Extracted from the intestinal mucosa of pigs, naturally occurring heparin is a polydisperse linear polymer composed of uronic acid and glucosamine disaccharide repeating units with an average molecular weight of 15,000 Daltons. In particular, the disaccharide 2-O-sulfo-α-L-iduronate-(1→4)-α-D-glucosamine-N, 6-O-disulfate-(1→4) accounts for 70 to 90% of disaccharide units in heparin (*Essentials of Glycobiology*. Second ed.; Gold Spring Harbor Laboratory: Cold Spring Harbor, N.Y., 2009), having the structure:

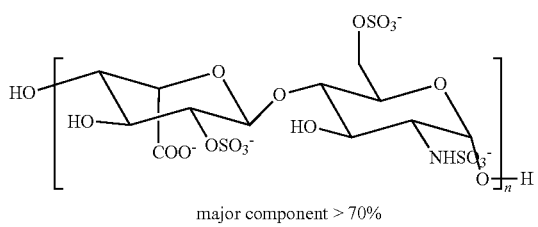

major component > 70%

Heparin biosynthesis occurs in the Golgi apparatus through a series of non-template enzymatic steps, resulting in a mixture of sulfated polysaccharides with varied molecular sizes and chemical compositions. In theory, 32 possible disaccharides exist in the building block so a dodecasaccharide fragment of heparin could be constituted of millions of species with many substitutions having the structure:

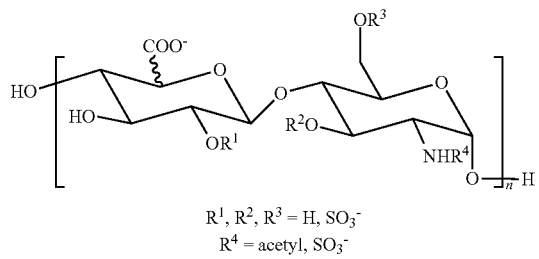

$R^1, R^2, R^3 = H, SO_3^-$
$R^4 = $ acetyl, $SO_3^-$

Also, there is some degree of structural similarity between different types of GAGs. These complexities render accurate analysis of heparins beyond the reach of current analytical technologies and detecting the GAG contamination or impurities in medicinal heparin remains a challenge. Analysis of heparin samples poses considerable challenges to current analytical techniques due to varied compositions, charges, and polydispersity as well as structural similarities among GAGs. As a consequence, the 2007-2008 crisis of heparin contaminated by oversulfated chondroitin sulfate resulted in the death of more than 80 people in the United States alone. Thus, a rapid and cost-effective method for identifying heparins and their analogous GAGs is sorely needed for the routine detection. At present, nuclear magnetic resonance (NMR) is the most effective technique capable of unambiguously identifying positions of the sulfates and one of the US pharmacopoeia approved methods for detecting traces of oversulfated chondroitin sulfate in heparin, but is limited to the analysis of low molecular weight and highly homogeneous heparins. Mass spectrometry (MS) based hyphenated methods like liquid chromatography (LC)-MS and capillary electrophoresis (CE)-MS are also commonly used techniques for the separation and identification of heparins. However, mass analysis is ineffective for distinguishing between isobaric isomers, which commonly exist in GAGs. Both LC and CE are also limited by their resolvability of a mixture of charged isomers.

To handle the complexity of heparins is beyond the capacity of current analytical technologies, such as mass spectrometry. Although heparin has been used medically since 1935, a simple set of standards for its identity and purity has not existed. The risk of contamination or impurities remains a great threat to the safety of the medicine. A crisis of heparin contaminated by oversulfated chondroitin sulfate resulted in the death of more than 80 people in the United States alone in 2007 and 2008 (Termblay, J. F. "Making Heparin Safe". *C&EN* (2016), 94, 30-34). Even after the event, the safety of heparin cannot be assured.

Nanopores, orifices with nanometer diameters and depth, have been used for biomolecule analysis (Im, J. et al. Electronic single-molecule identification of carbohydrate isomers by recognition tunnelling. (2016) *Nat. Commun.* 7, 13868), such as DNA sequencing, where steps in the ion current are associated with sequences of nucleotide blocks. Nanopores are typically composed of or fabricated from biological or inorganic materials (Dekker, C. Solid-state nanopores. (2007) *Nat. Nanotechnol.* 2:209-215) and have been exploited as a single molecule sensor for analysis of DNA, RNA, proteins, and polysaccharides (Karawdeniya, B. I., et al (2018) *Nat. Commun.* 9:3278). Short unsulfated glycosaminoglycan hyaluronan translocated through an aerolysin nanopore (Fennouri, A. et al, *ACS nano* 2012, 6:9672-9678) and glycans through a solid state nanopore (Takemasa, M. et al, *Proceedings of the Interantional Conference*, Edel, J.; Albrecht, T., Eds. RSC Publishing: UK, 2012; pp 89-92). The nanopore have not been used to identify heparin or sulfated glycosaminoglycans (GAGs) on a single molecule basis. On the other hand, machine-learning methods have been used to extract additional information from ionic current signals, notably from DNA hairpins (Vercoutere, W. et al, *Nat. Biotechnol.* (2001) 19:248-252) and to extract structural information from t-RNAs (Henley, R. Y. et al, *Nano Lett* 2016, 16, 138-44) as well as to improve the accuracy of sequence data from the Minion nanpore DNA sequencer (Boza, V. et al, *PLoS One* 2017, 12, e0178751). SVM is a supervised learning model to separate different classes in a hyperdimensional space (Winters Hilt, S. & Akeson, M. (2004) *DNA Cell Biol.* 23:675-683). SVM has been used to identify mono- and di-saccharides by classifying their electron tunneling data (Im, J. et al. (2016) *Nat. Commun.* 7:13868). However, the problems of identifying specific heparins are much more complicated than those with nucleic acids or other biomolecules. These are mixtures with polydisperse molecule weights and charges. It is therefore not apparent that a machine learning analysis of nanopore currents could be used to identify heparins and other glycosoaminglycans, and do so with high sensitivity, over a large range of concentrations.

SUMMARY

The present disclosure provides methods and apparatuses for identification of heparins and other glycosaminoglycans (GAGs) with reference to their standard samples, thus enabling facile quality control. The present disclosure further provides means of detecting and quantifying small volume (microliter) samples down to nanomolar concentrations. The present disclosure further provides methods for identifying impurities in a sample down to the 0.5% level or better. In certain embodiments, the disclosed methods and apparatuses achieve five decades of magnitude in concentration.

The invention provides a nanopore device for detection of sulfated glycosaminoglycans without labeling. It provides a quick and cheap method for pharmaceutical companies to monitor the contamination in the heparin drugs and for clinics to monitor the heparin level in patient's blood.

In one aspect, the disclosure provides a method for characterizing the purity of glycosaminoglycans, comprising:

(a) passing one or more calibration samples through a first nanopore while recording a current signal;

(b) passing a glycosaminoglycan sample to be characterized through the first nanopore or a second nanopore; and (c) using a machine learning algorithm to determine the purity of the glycosaminoglycan sample to be characterized.

In another aspect, the disclosure provides a method for characterizing the purity of glycosaminoglycans, comprising:

(a) passing one or more calibration samples through a first silicon nitride nanopore while recording a translocation current signal;

(b) passing a negatively charged glycosaminoglycan sample to be characterized through the first silicon nitride nanopore or a second silicon nitride nanopore while recording a translocation current signal; and (c) using a machine learning algorithm to determine the purity of the negatively charged glycosaminoglycan sample to be characterized from the translocation current signals.

DESCRIPTION OF THE DRAWINGS

FIG. 1A shows a schematic illustration of a solid-state nanopore device for translocation of linear negatively charged polysaccharides (the cis-side electrode is grounded).

DEFINITIONS

Figure 1B:
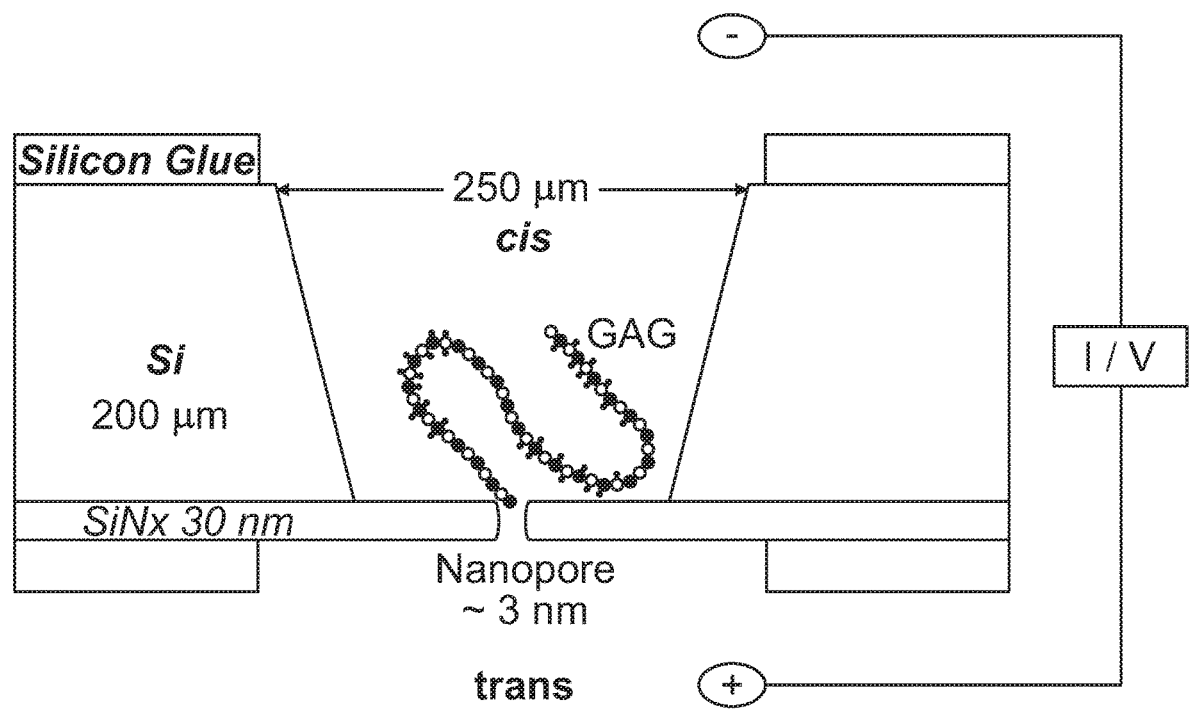
FIG. 1B shows ionic current traces of $HP_{dp20}$ and $CS_{dp20}$ translocating through a nanopore.
Figure 1B:
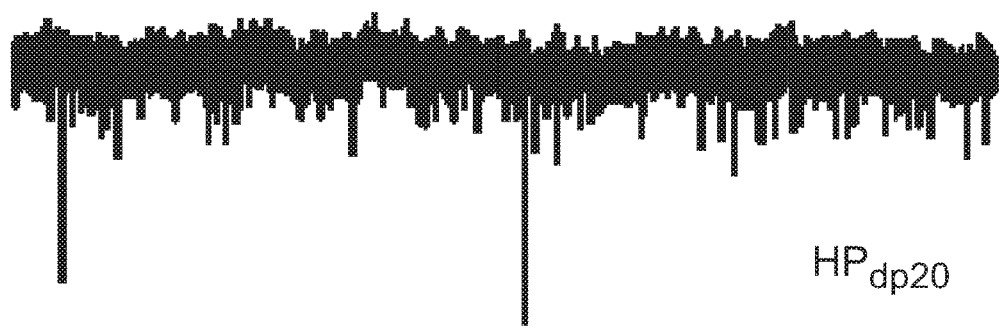
Figure 1B:

"Glycosaminoglycans" (GAGs) or mucopolysaccharides are long unbranched polysaccharides consisting of a repeating disaccharide unit. The repeating unit (except for keratan) consists of an amino sugar (N-acetylglucosamine or N-acetylgalactosamine) along with a uronic sugar (glucuronic acid or iduronic acid) or galactose. Glycosaminoglycans are highly polar and attract water.

A "calibration sample" is a reference sample, for analysis of known identity and concentration.

A "nanopore" is an orifice with nanometer diameter and depth in a solid material. The nanopore shape may be irregular and change according to conditions and use, or the nanopore may be fixed in dimensions and may be a regular shape such as circular. One or more nanopores may be assembled in a device to measure electrical signals such as current and voltage.

"Machine learning" is a statistical technique to iteratively refine and improve models by which raw data can be classified and used to make predictions on data.

A "Support Vector Machine" or "SVM" refers to a supervised learning model to separate different classes in a hyperdimensional space and is a type of machine learning algorithm, used here as a tool of analyzing data from single molecule detection.

DETAILED DESCRIPTION OF EXEMPLARY EMBODIMENTS

The invention provides a nanopore and SVM (support vector machine) method to identify, quantify, and characterize heparins and chondroitin sulfate, which represent a class of polysaccharides that pose great challenges to current analytical techniques for their separation and identification due to their varied compositions, charges, and polydispersity. Chondroitin sulfate is a sulfated glycosaminoglycan (GAG) composed of a chain of alternating sugars (N-acetylgalactosamine and glucuronic acid) and is usually found attached to proteins as part of a proteoglycan. A chondroitin chain can have over 100 individual sugars, each of which can be sulfated in variable positions and quantities. Chondroitin sulfate is an important structural component of cartilage.

The solid-state nanopore is one of the simplest single molecule sensor and SVM is a machine learning algorithm. By combining these two together, heparins and chondroitin sulfate can be identified with high accuracy (>90%) and quantified with high accuracy. Chondroitin sulfate can be identified in a mixture with the heparin to a level as low as 0.8% (w/w). The data indicates that the nanopore/SVM method has potential to identify an impurity present at as low as about 0.5 to 0.05% (molar ratio). In addition, data shows that the nanopore has a limit of detection about 1.0 nanomolar (nM) and 5 decades of magnitude in dynamic range. Also, the nanopore/SVM technique distinguished between unfractionated heparin (UFH) and enoxaparin with an accuracy of about 94% on average. Using a reference sample to calibrate nanopores, heparin is quantified using different nanopores with reasonable accuracy, achieving nanomolar sensitivity and a 5-Log dynamic range, demonstrating that the nanopore/SVM technique can be used to monitor heparins and identify GAGs. These results show that the nanopore technique powered by machine learning can be a simple and cheap tool for monitoring heparins and other glycosaminoglycans (GAGs) from lot to lot with reference to standard samples that are fully characterized by NMR, mass spectrometry, and other analytic methods.

Figure 1C:
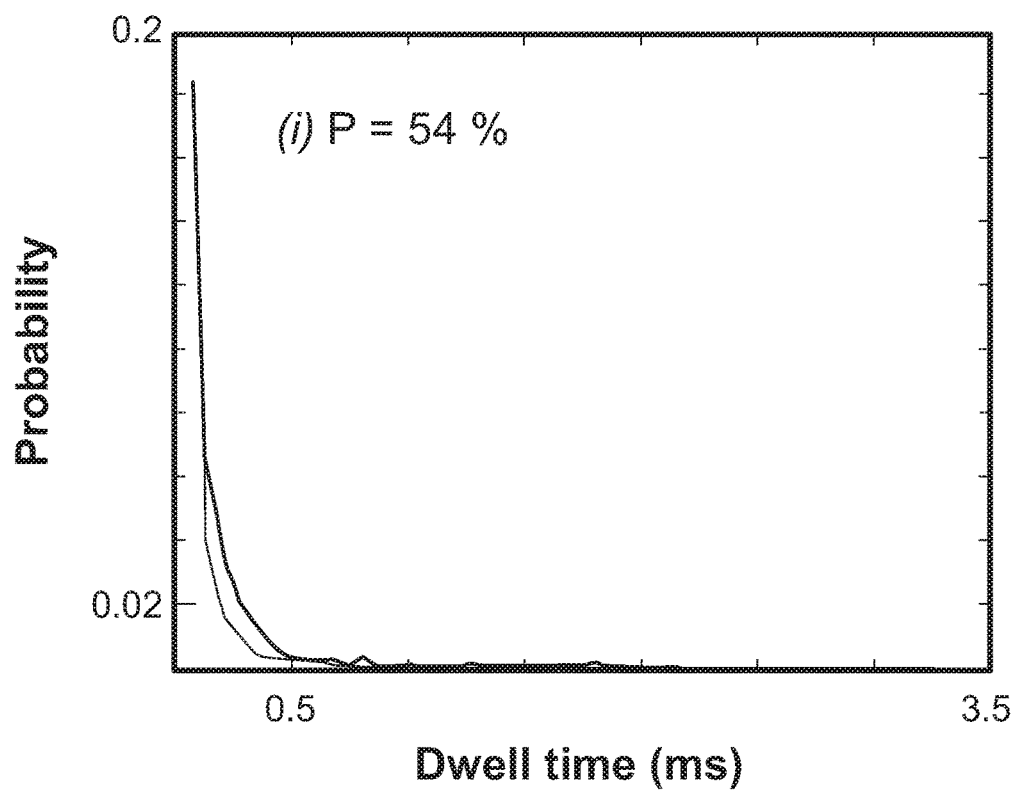
FIG. 1C shows a one-dimensional plot of distributions of dwell time for $HP_{dp20}$ and $CS_{dp20}$.
Figure 1D:
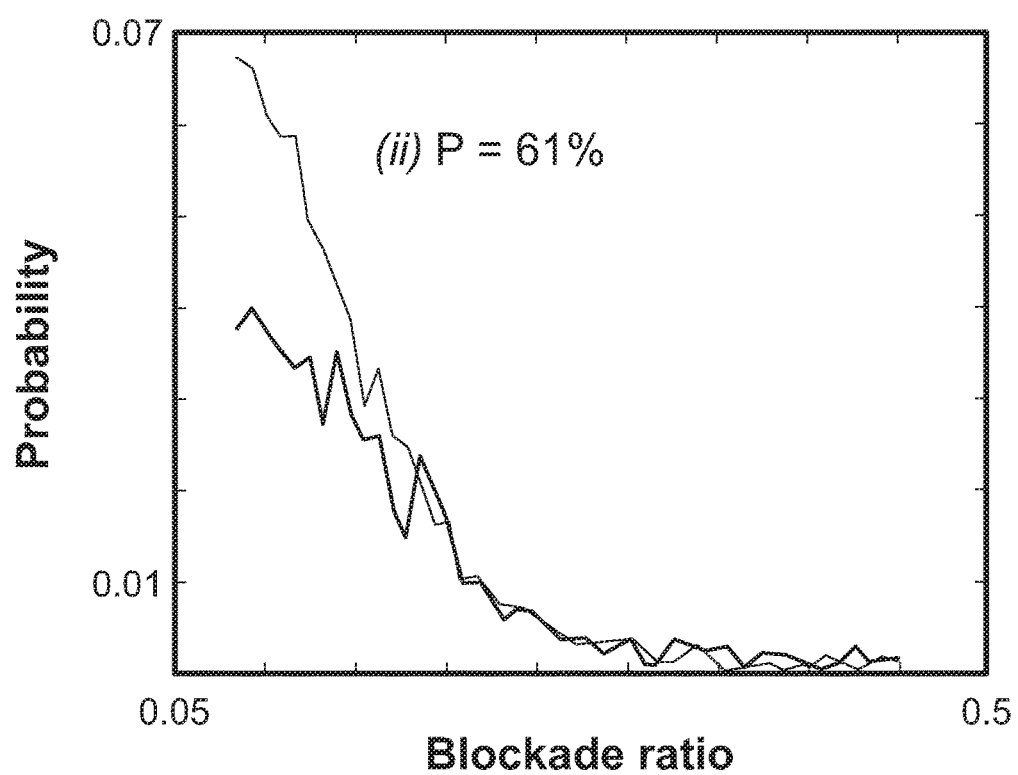
FIG. 1D shows a one-dimensional plot of distributions of blockade for $HP_{dp20}$ and $CS_{dp20}$.

The present invention employs a silicon nitride nanopore for differentiation between GAGs, such as two sulfated GAGs; heparin and oversulfated chondroitin sulfate (OSCS). Both heparin and OSCS in a mixture can be qualitatively identified either by current blockade magnitudes or blockade durations despite considerable overlaps of these parameter distributions in a 2D scatter plot. Nanoelectronic technologies are useful for the identification and sequencing of carbohydrates. Solid-state nanopores can be used to distinguish heparins from chondroitin sulfate on a single molecule basis with the aid of machine learning, and the frequency of translocation signals can be used for heparin quantitation over a wide dynamic range. As illustrated in FIG. 1A, when a negatively charged GAG molecule translocates through a silicon nitride nanopore under a voltage bias, it can cause a transient blockade of ionic current, generating a spike; an event that carries information on the structure and physical properties of the GAG molecule as it interacts with the nanopore. FIG. 1B shows current traces of monodispersed heparin ($HP_{dp20}$) and chondroitin sulfate ($CS_{dp20}$) fragments generated by nanopore measurements. Herein, $HP_{dp20}$ denotes a heparin fragment that is composed of 20 sugar units (dp: degree of polymerization), and $CS_{dp20}$ chondroitin sulfate fragment that is comprised of 10 disaccharide units of β-D-glucuronic acid-(1→3)-β-N-acetylgalactosamine-4-sulfate (1→4) (Lamari, F. N. & Karamanos, N. K. in Chondroitin Sulfate: structure, role and pharmacological activity, Vol. 53. (eds. J. T. August, D. Granner & F. Murad) 33-48 (2006) Elsevier Inc.). Each individual signal was characterized by its blockade ratio (of the spike amplitude to baseline ionic-current) and dwell time (width of the spike). Each of these individual parameters exhibited similar distributions between $HP_{dp20}$ and $CS_{dp20}$. As shown in FIGS. 1C and 1D, the probability of separating $HP_{dp20}$ from $CS_{dp20}$ by their dwell times is about 54%, and the probability by their blockade ratios is about 61% (slightly better than a random pick that is 50%). When these two parameters are plotted together as the probability density for the simultaneous appearance of a pair of values in a given spike, it improves the separation to >66%. Higher accuracy may be achieved in a high dimensional space to classify the nanopore data with the use of machine learning for analysis of the nanopore data, engaging Support Vector Machines (SVMs). SVM is a supervised learning model to separate different classes in a hyperdimensional space and is used here as a tool of analyzing data from single molecule detection. SVM is employed here to analyze solid-state nanopore translocation data of GAG molecules.

Identification of heparins and related GAGs:

Heparin, a member of a group of sulfated glycosaminoglycans (GAGs) has the repeating structure:

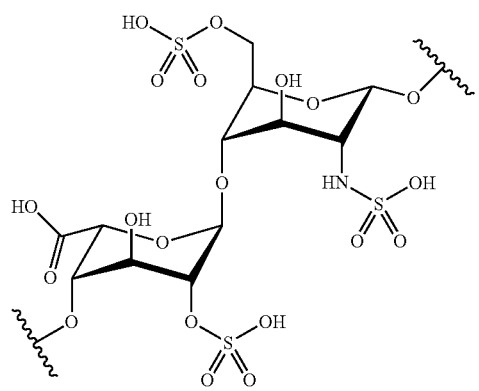

Heparin (CAS Reg. No. 9005-49-6) has a molecular weight of about 12,000-15,000 and is a naturally occurring anticoagulant produced by basophils and mast cells. In therapeutic doses, it acts as an anticoagulant, preventing the formation of clots and extension of existing clots within the blood.

Heparins were identified using a nanopore device (FIG. 1A). The ionic current blockages of both $HP_{dp20}$ and $CS_{dp20}$ were measured in a nanopore using the device shown in FIG. 1A, generating translocation current signals. When the GAG molecules translocate through the silicon nitride nanopore, they transiently block the ionic current and produce spikes that can be recorded as a signal train with time. FIG. 1B shows spectra of current traces generating by translocation of a monodisperse heparin (HP) fragment designated as $HP_{dp20}$, which is composed of 20 sugar units (dp: degree of polymerization), and a GAG counterpart, chondroitin sulfate ($CS_{dp20}$) that is composed of 10 disaccharide units of sulfated β-D-glucuronic acid-(1→3)-β-N-acetylgalactosamine-(1→4) (Lamari, F. N.; Karamanos, N. K. Structure of Chondroitin Sulfate. In *Chondroitin Sulfate: Structure, Role and Pharmacological Activity*, August, J. T.; Granner, D.; Murad, F., Eds. Elsevier Inc.: 2006; Vol. 53, pp 33-48). Although these two GAGs are composed of monodisperse oligosaccharides, they contain different sulfation patterns, respectively.

Nanopore/SVM Identification of $HP_{dp20}$ and $CS_{dp20}$.

Figure 2A:
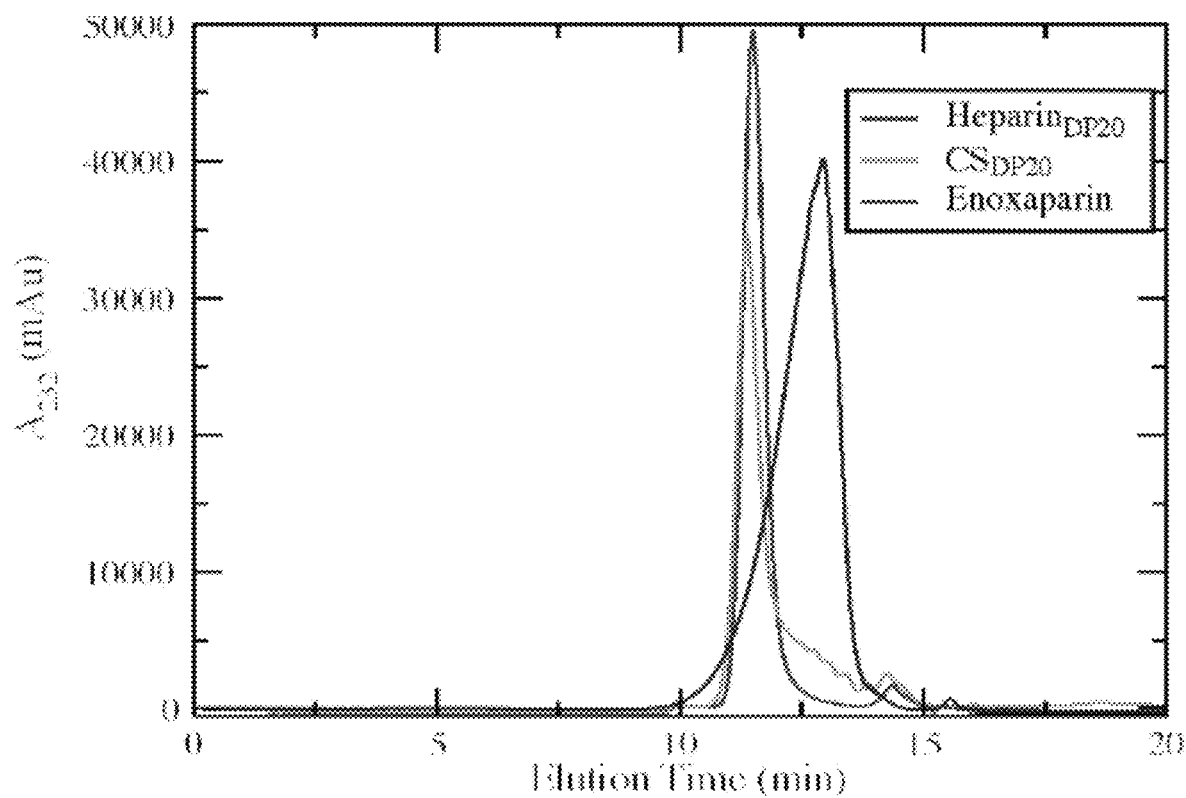
FIG. 2A shows Size Exclusion (SE)-HPLC chromatogram of Heparin ($HP_{DP20}$), Chondroitin ($CS_{DP20}$) and enoxaparin. Heparin has the larger maxima at about 11.8 mins. Chondroitin has a smaller maxima at about 11.8 mins. Enoxaparin has a maxima at about 13 mins. The analysis was carried out on an Agilent PL aquagel-OH 20 column (300 mm×7.5 mm). 0.2 mg of each polysaccharide was applied to the column and eluted with an isocratic flow of 1 mL/min. The mobile phase is 0.5 M NaCl, 5 mM Phosphate, pH 4.
Figure 2B:
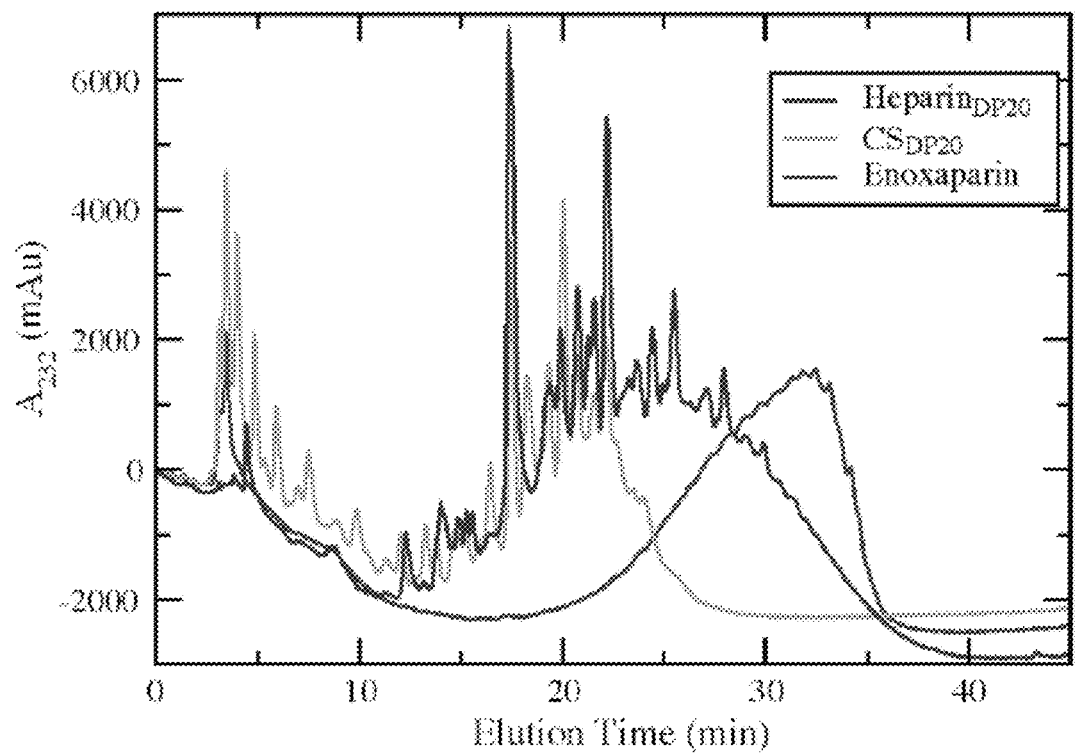
FIG. 2B shows Strong Anion-Exchange (SAX)-HPLC chromatogram of HPDP20, $CS_{DP20}$ and enoxaparin. The analysis was carried out on a Waters Spherisorb SAX column (250 mm×4.6 mm). 0.2 mg of each polysaccharide was applied to the column and eluted with a NaCl gradient of 0.45 M to 1.5M at pH 2. Flow rate is 1 mL/min. Heparin has the darker line profile with sharp peaks at about 17.5 and 21 minutes. Chondroitin ($CS_{DP20}$) is the lighter line profile with sharp peaks at about 4, 17.5 and 20 minutes. Enoxaparin has a broad peak from about 25-34 minutes.
Figure 3A:
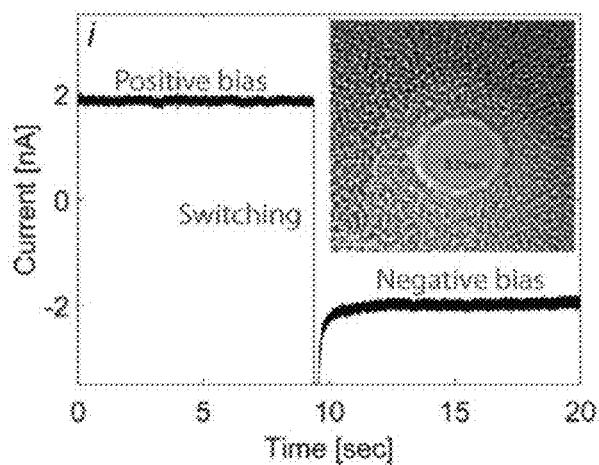
FIG. 3A shows reversing bias experiment with a transmission electron microscope (TEM) image of the nanopore. The ionic current was recorded under a 400 mV voltage bias. The ionic current traces in a PB buffer containing 400 mM KCl, pH 7.4 with the electrode in the Trans chamber at positive polarity and negative polarity.
Figure 3B:
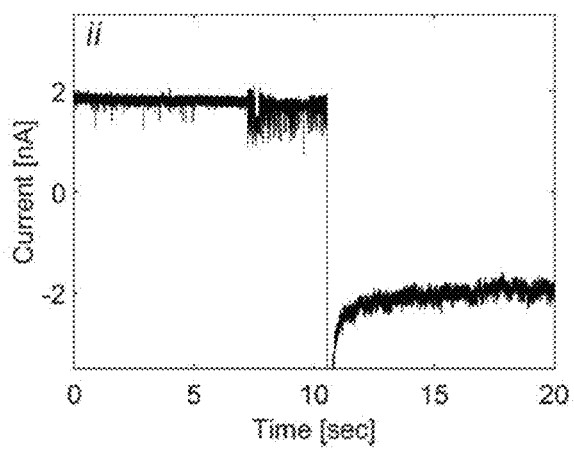
FIG. 3B shows ionic current traces measured right after injected with a HPdp20 solution at 1.0 µM concentration in the Cis chamber. GAG samples injected into the cis chamber translocate through the pore into the trans chamber under the force of the electric bias.
Figure 3C:
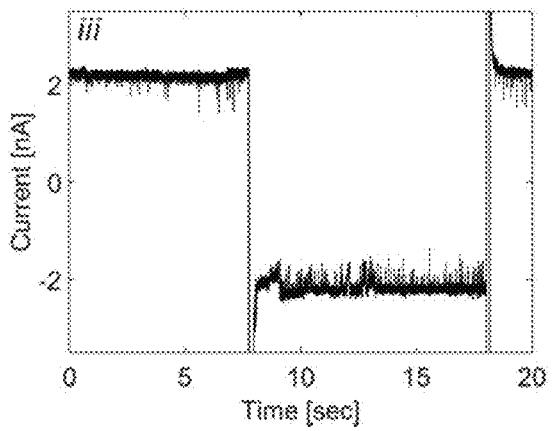
FIG. 3C shows ionic current traces measured after applying 600 mV.
Figure 4A:
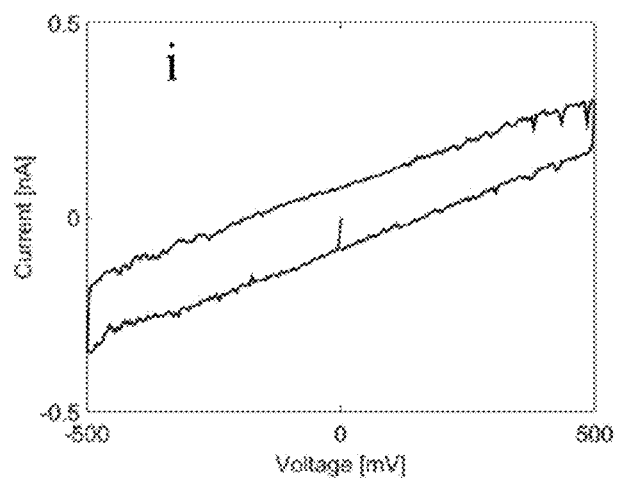
FIG. 4A shows a typical I-V response of a silicon nitride nanopore drilled by transmission electron microscope (TEM) in 10 mM KCl, PB buffered solution with pH=6.5, at which a rectified ion current can be perceived. The Current-Voltage (I-V) response is an ionic current change with voltage across the membrane.
Figure 4B:
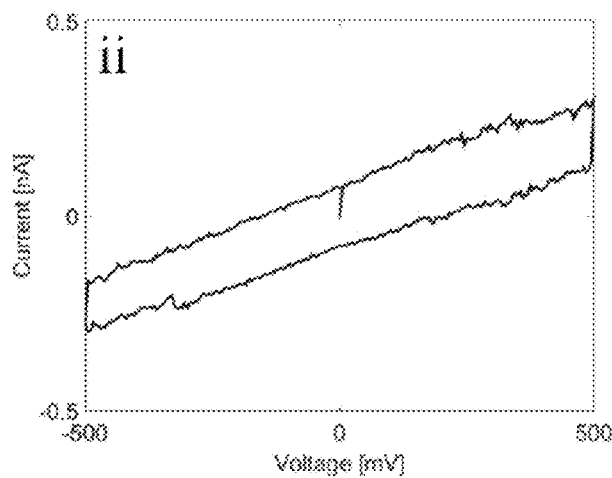
FIG. 4B shows a typical I-V response of a silicon nitride nanopore drilled by TEM in 10 mM KCl, PB buffered solution with pH=7.5, at which a rectified ion current can be perceived.
Figure 4C:
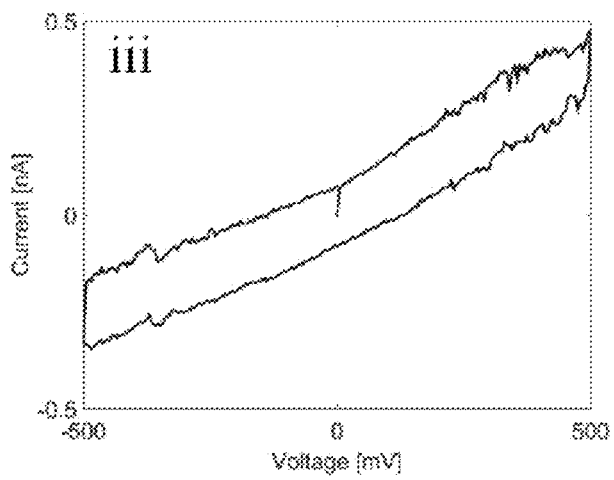
FIG. 4C shows a typical I-V response of a silicon nitride nanopore drilled by TEM in 10 mM KCl, PB buffered solution with pH=8.5, at which a rectified ion current can be perceived.
Figure 5A:
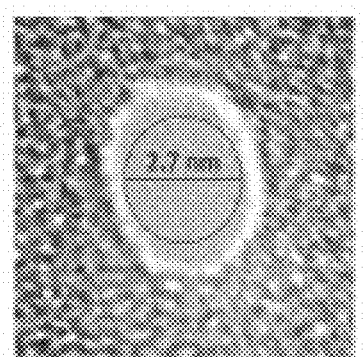
FIG. 5A shows a TEM image of the solid-state nanopore in the silicon nitride membrane for measurement of GAGs.

Monodisperse GAG samples $HP_{dp20}$ and $CS_{dp20}$ were characterized by size exclusion (FIG. 2A) and anion-exchange HPLC (FIG. 2B). Both have similar molecular weights, but $HP_{dp20}$ is more negatively charged than $CS_{dp20}$. Density Functional Theory (DFT) modeling shows that the most common disaccharide units in heparin and CS have distinct structural features, but both of them are highly negatively charged. DFT is a computational quantum mechanical modelling method used in physics, chemistry and materials science to investigate the electronic structure (principally the ground state) of many-body systems, in particular atoms, molecules, and the condensed phases. These differences in their electrical properties enable the nanopore to distinguish between $HP_{dp20}$ and $CS_{dp20}$. The solid-state nanopores were fabricated in a silicon nitride membrane by drilling with a transmission electron microscope (TEM), most likely generating an hourglass-shaped geometry (Kim, M. J., et al (2007) *Nanotechnology* 18:205302). Given that the surface of silicon nitride is zwitterionic with an isoelectric point around pH 7, these nanopores should have their surface charges close to neutral in a buffer, pH=about 7.4, at which the translocation experiments were carried out. Around the pH value, rectified currents were not clearly observed (FIGS. 4A-C). By a reversing bias experiment, FIG. 3B shows that $HP_{dp20}$ was able to translocate through a solid state nanopore. It may be an indicator of a neutral surface because the rectification requires an asymmetric electrical double layer within the nanopore. In a 0.4 M KCl electrolyte solution buffered with 1.0 mM phosphate buffer, pH 7.4, the nanopore generated a 2 nA ionic current with a stable baseline (FIG. 3A). Switching the bias from the positive to negative changed the current polarity and slightly increased the width of the baseline. When a $HP_{dp20}$ solution was injected with a 1.0 μM final concentration of 1.0 μM in the cis-chamber of the nanopore where the electrode was grounded, frequent current blockade events (spikes) were observed under a positive bias, but no blockade signals under a negative bias (FIG. 3B). A 600 mV bias was applied for two hours and the ionic current was measured again. Blockage signals were observed from both positive and negative biases (FIG. 3C). These results can best be explained by $HP_{dp20}$ molecules being translocated from the cis to trans chamber through the nanopore. In general, a thinner nanopore should give better resolution, but is more fragile than a thicker one. After comparing the translocation in nanopores with different thickness (15, 30, and 50 nm), a 30 nm thick silicon nitride membrane was selected for its easy of handling and less probability of multi-molecule blockade (FIGS. 3A-C). Also by a reverse bias experiment, it was confirmed that $HP_{dp20}$ translocated through a solid-state nanopore of about 3.0 nm in diameter (FIGS. 3A-C). Following this benchmark work, serial measurements on $HP_{dp20}$ and $CS_{dp20}$ with a newly fabricated silicon nitride nanopore. FIG. 5A shows the transmission electron microscope (TEM) image of a nanopore.

Figure 5B:
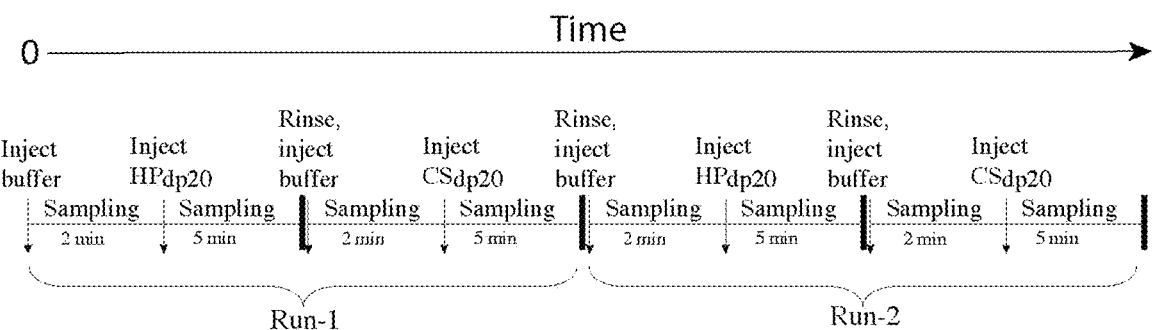
FIG. 5B shows a work flow for a multiple run experiment measuring the GAGs translocation through nanopores, which was carried out in a phosphate buffer, pH 7.4.
Figure 5C:
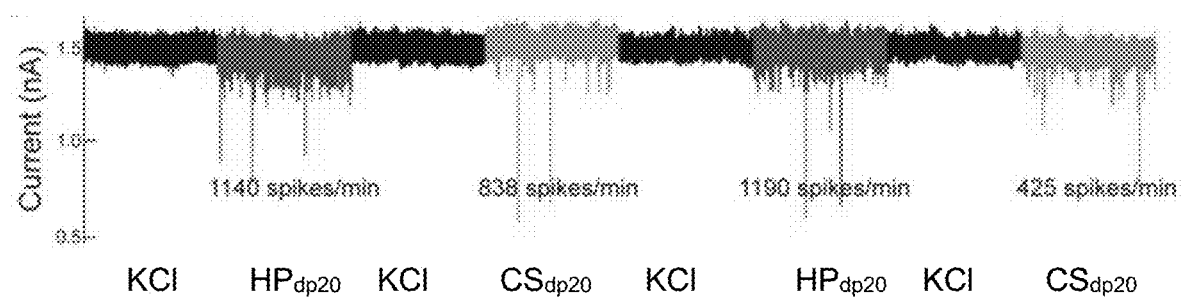
FIG. 5C shows typical ionic current traces for 0.4 M KCl, $HP_{dp20}$, and $CS_{dp20}$ samples and their current spike rates, recorded with a voltage bias of 500 mV.

FIG. 5B shows a work flow for the translocation measurements of analytes. It begins with running a PBS buffer, followed by injecting first sulfated GAG (here it is $HP_{dp20}$), second sulfated GAG (here it is $CS_{dp20}$), and then rinse the nanopore to finish the first run (Run-1). The process is repeated in the second run (Run-2) either with the same samples or with samples to be tested. In general, the first run samples can be standard samples and second ones can be those to be analyzed. As illustrated in FIG. 5B, the two GAG samples were sequentially measured in Run-1 and Run-2. Note that there was a process of rinsing the nanopore and stabilizing (or recovering) the baseline prior to measuring each of the samples. FIG. 5C displays traces of ionic currents recorded from each discrete measurements of 0.4 M KCl, $HP_{dp20}$, and $CS_{dp20}$, where each spike may represent a single molecule translocating or bumping event, a "translocation current signal". At first glance, $HP_{dp20}$ shows higher event rates than $CS_{dp20}$, and the event rates of $CS_{dp20}$ varied more significantly than those of $HP_{dp20}$ from run to run. Nanopore data was analyzed by dwell times and blockade ratios of individual spikes, and plotted in histograms shown in FIGS. 5D and 5E, respectively. The distributions of dwell times were best fit to the Lognormal function, whereas those for blockade ratios were best fit to the Gaussian function, from which statistical values of these parameters were derived for both $HP_{dp20}$ and $CS_{dp20}$ and summarized in Table 1. These parameters are only marginally different from Run-1 to Run-2 for both $HP_{dp20}$ and $CS_{dp20}$, indicating that the nanopore measurement is reasonably reproducible. Statistically, each parameter distribution shows significant overlap between $HP_{dp20}$ and $CS_{dp20}$ (see FIGS. 5D and 5E). These primary parameters are not sufficient for discriminating among monodisperse GAG samples unambiguously.

TABLE 1

Figure 5D:
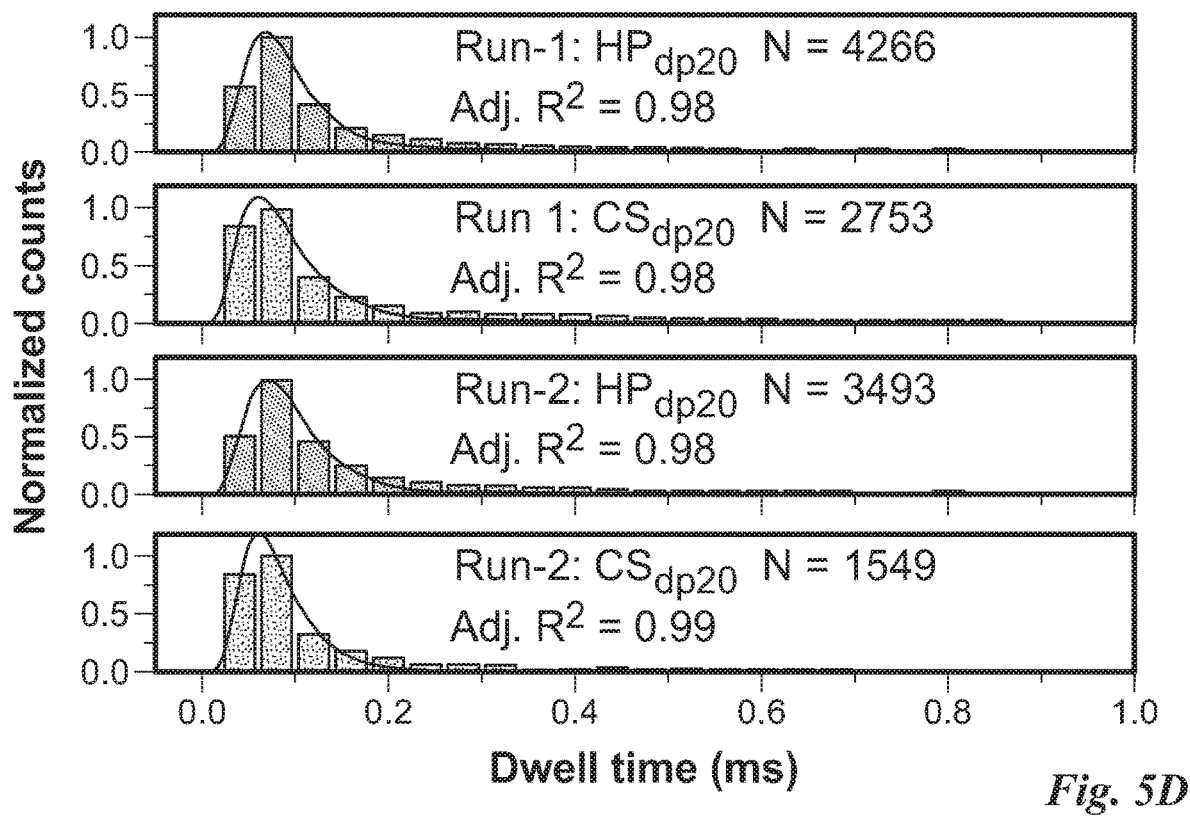
FIG. 5D shows histograms of dwell times with their Lognormal fitting curves for $HP_{dp20}$ and $CS_{dp20}$ at different runs.
Figure 5E:
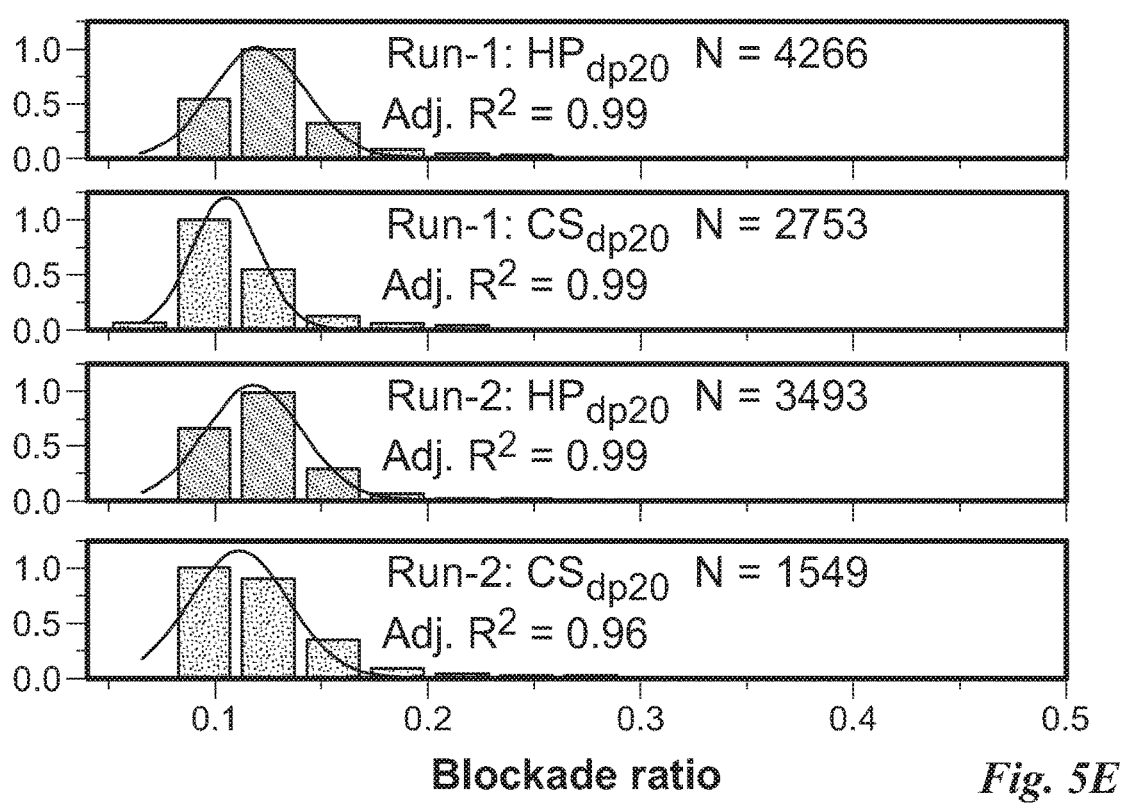
FIG. 5E shows Histograms of blockade ratios with their Gaussian fitting curves for $HP_{dp20}$ and $CS_{dp20}$ at different runs.

Statistical parameters derived from curve fitting of raw data in FIGS. 5D and 5E

| | $HP_{dp20}$ | | | | $CS_{dp20}$ | | | |
|---|---|---|---|---|---|---|---|---|
| | Dwell Time (ms) | | Blockade Ratio | | Dwell Time (ms) | | Blockade Ratio | |
| | Median | Mean | Mean | σ | Median | Mean | Mean | σ |
| Run-1 | 0.083 | 0.092 | 0.120 | 0.027 | 0.080 | 0.092 | 0.105 | 0.019 |
| Run-2 | 0.087 | 0.098 | 0.118 | 0.027 | 0.073 | 0.081 | 0.111 | 0.028 |

Figure 6:
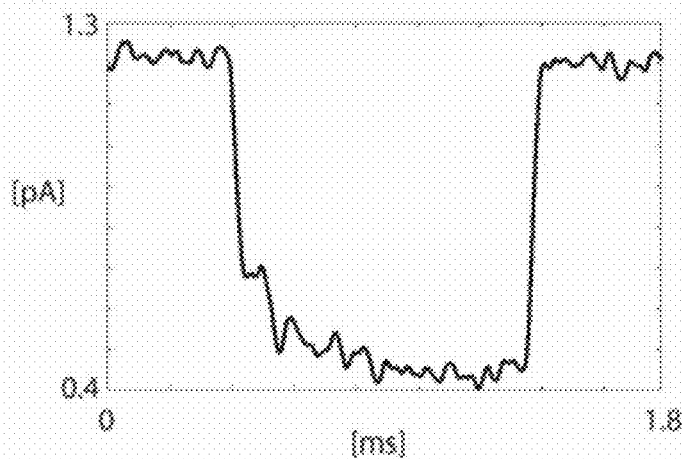
FIG. 6 shows feature extraction in three domains.
Figure 6:
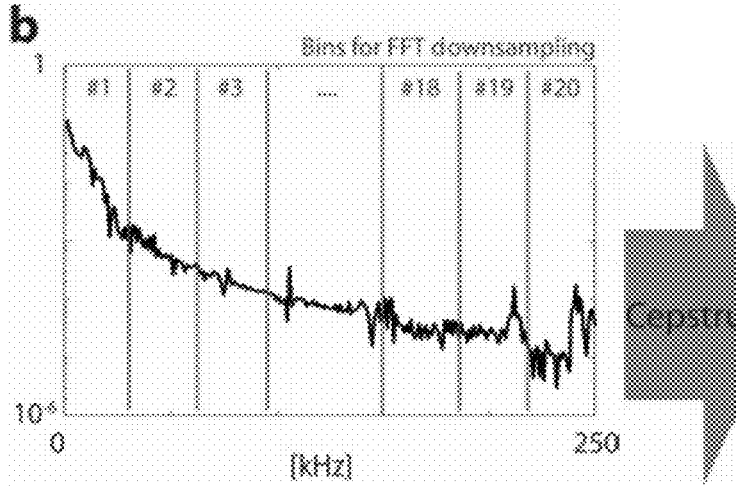
Figure 6:
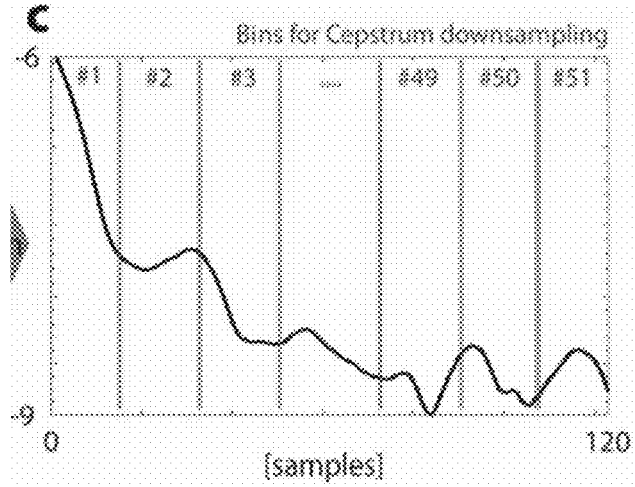

Note:
(1) all adj. $R^2$ >95%;
(2) all fitting errors for median <±1.0% and for mean <±1.0%;
(3) all fitting errors for Peak <±0.1% and for Width <±0.2%.
ms = milliseconds Machine learning, particularly SVM, was used to analyze the translocation current signals of the nanopore data. SVM is a method that requires many independent parameters (or features) to classify data in a hyperdimensional space. A plethora of features were extracted by Fourier transform (FFT) and cepstrum transform of the nanopore data recorded in the time domain to index individual spikes (FIG. 6). A cepstrum is the result of taking the Inverse Fourier transform (IFT) of the logarithm of the estimated spectrum of a signal. For the machine learning, 50% of the nanopore data was randomly taken either from Run-1 or Run-2 to train SVM until it could successfully assign each of the spikes in the training data to its corresponding GAG analyte with 100% accuracy (Table 2). SVM could be trained with different combinations of features, as a trained machine learning algorithm, to achieve the same 100% accuracy, i.e. many different SVMs can be created using the same data set (Example 3, Table 11). To score, these trained SVMs were engaged to call the remaining 50% of the randomly selected nanopore data by scaling a perfect calling accuracy to 100%. As shown in Table 2, SVM-2 has the highest rating of 92.7 among those trained with the Run-1 data, and SVM-4 has the highest score of 95.1 among those trained with the Run-2 data on average. SVM-2 was used to call the Run-2 data, which identified $HP_{dp20}$ and $CS_{dp20}$ with an accuracy of 94.2% and 95.1%, respectively. Similarly, SVM-4 called $HP_{dp20}$ and $CS_{dp20}$ in the Run-1 data with an accuracy of 93.7% and 91.2%, respectively. In either instance, SVM called these two GAGs with high accuracy. It should be noted: (1) the accuracy is related to SVM calling single spikes. Assuming the errors occur randomly, one may expect that it can be further improved by multiple nanopore measurements; (2) the nanopore data may be a sum of molecular bumping and translocating events. The above results suggest that both bumping and translocating data can be used by the SVM to identify the GAG molecules.

TABLE 2

Accuracy of SVM calling individual spikes

| | SVM Training | | | | | SVM Calling | | | |
|---|---|---|---|---|---|---|---|---|---|
| | Training data set | Analyte | No. Features | Training accuracy | Remaining 50% data | | | Untrained data | |
| | | | | | $HP_{dp20}$ | $CS_{dp20}$ | | $HP_{dp20}$ | $CS_{dp20}$ |
| SVM-2 | 50% of Run-1 | $HP_{dp20}$ $CS_{dp20}$ | 11 | 100 | 93.2 6.8 | 7.9 92.1 | Run-2 | 94.2 5.8 | 4.9 95.1 |
| SVM-4 | 50% of Run-2 | $HP_{dp20}$ $CS_{dp20}$ | 11 | 100 | 96.2 3.8 | 6.0 94.0 | Run-1 | 93.7 6.3 | 8.8 91.2 |

Detection of $CS_{dp20}$ in a binary mixture.

The nanopore/SVM method was tested for its potential use in the detection of impurities in a heparin product. $CS_{dp20}$ was mixed with $HP_{dp20}$ in a molar percentage of 1%, 5%, 10%, 20%, and 50%, respectively. The nanopore measurement was carried out in the same way as described above, following a sequence of $CS_{dp20}$, $HP_{dp20}$, and the mixture. Here, the pure $CS_{dp20}$ and $HP_{dp20}$ samples were used as standards to produce the reference data for training SVM. The nanopore was easily blocked by these mixtures presumably during the translocation process. However, the measurements were also conducted using multiple nanopores. As shown in Table 3, six nanopores were used in this study, and each mixture was measured at least twice either by the same nanopore or different nanopores.

Figure 7A:
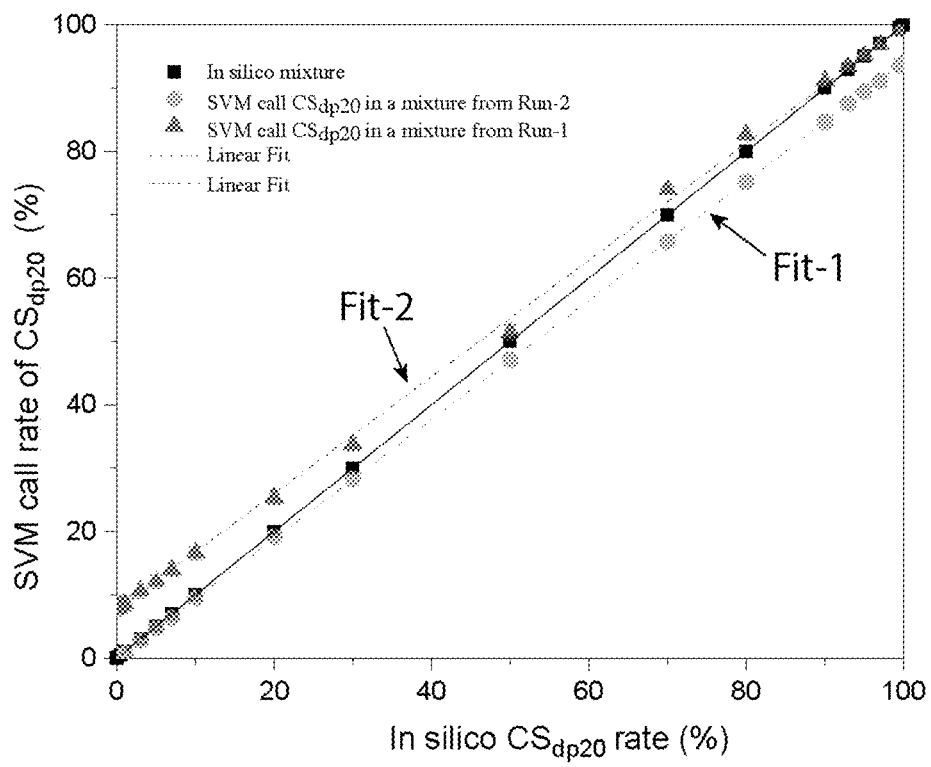
FIG. 7A shows SVM (support vector machine) determination of $CS_{dp20}$ and $HP_{dp20}$ compositions of simulated test mixtures. The simulated results are randomly sampled with a certain CS20 ratio from data pool, and tested SVM to compare the result ratio with respect to the desired ratio from two runs with the same nanopore.
Figure 7B:
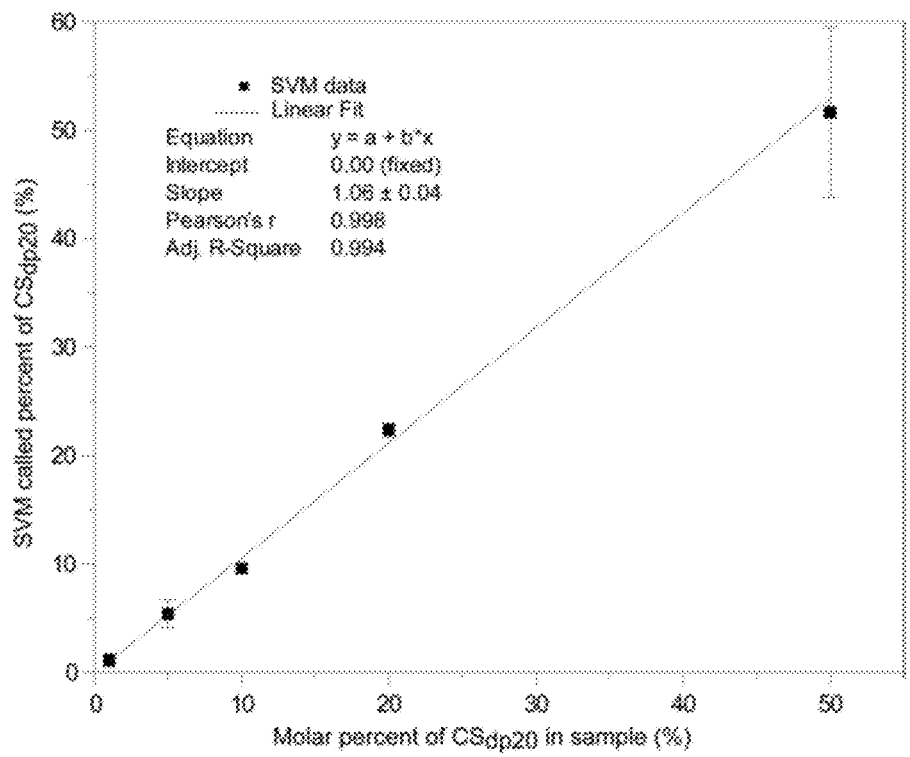
FIG. 7B shows percentages of $CS_{dp20}$ determined by nanopore/SVM method against its compositions in the mixture samples as determined from experimental data with several different nanopores.

Following the nanopore measurement, SVM with data from the reference samples was trained in the same manner as described above and engaged the SVMs to call $HP_{dp20}$ and $CS_{dp20}$ in the mixtures from their nanopore data (Table 4). Table 4 lists the percentages of $CS_{dp20}$ in the different mixtures determined by the best-scored SVM. Although the measured percentage of $CS_{dp20}$ varies more or less from nanopore to nanopore, which may be attributed to the variations in the geometry of nanopores, the average is close to the correct percentage existing in the mixture. A plot of the average called percentages against molar percent of $CS_{dp20}$ in the mixtures fits a linear function (FIG. 7B). With its intercept fixed at the origin, the fit gives the trendline a slope of about 1.1, slightly higher than 1.0 which is the best-case scenario, and which may result in an overestimate of $CS_{dp20}$ by 10%. Overall, the variations among different pores decrease with increases of $CS_{dp20}$ percentage in the mixture, as do the SVM calling error rates (based on CV values and error rates in Table 3). This study demonstrates the nanopore/SVM method can identify $CS_{dp20}$ in a mixture down to about 1% in molar percentage, equal to a weight percentage of 0.8% (w/w). This sensitivity is comparable to 500 MHz NMR, which has a limit of detection of 0.1% w/w for oversulfated chondroitin sulfate (OSCS).[39] However, NMR requires milligrams of sample/0.7 mL solvent for the measurement so that the OSCS ought to be at least at a microgram level in the sample. For the nanopore measurement, 0.1 mL of solution was used with the mixture containing a total GAG concentration of 100 nM. To measure the 1% mixture, only 0.4 ng of $CS_{dp20}$ was needed for the nanopore detection.

TABLE 3

$CS_{dp20}$ molar percentages in mixtures determined by the nanopore/SVM method

| Nanopore | SVM score | Molar percentage of $CS_{dp20}$ in $HP_{dp20}$ | | | | |
|---|---|---|---|---|---|---|
| | | 1% | 5% | 10% | 20% | 50% |
| | | Percentage (%) of $CS_{dp20}$ determined by SVM calling | | | | |
| Pore-1 | 98.3 | | | | | 46.1 |
| Pore-1[a] | 100 | | | | | 57.2 |
| Pore-2 | 93.3 | 1.4 | | 11.1 | | |
| Pore-3 | 94.0 | 3.0 | 7.4 | | | |
| Pore-4 | 84.1 | | | | 23.2 | |
| Pore-5 | 83.3 | 0.5 | 3.9 | | | |
| Pore-6 | 80.8 | | | 9.3 | 21.9 | |
| Average ± SEM[b] | | 1.6 ± 0.7 | 5.7 ± 1.8 | 10.2 ± 0.9 | 22.6 ± 0.7 | 51.7 ± 5.6 |
| CV (%)[c] | | 77.5 | 43.8 | 12.5 | 4.1 | 15.2 |
| Error rate (%)[d] | | 60.0 | 14.0 | 2.0 | 13.0 | 3.4 |

[a] a repeat of the measurement in Pore-1;
[b] SEM: standard error of mean;
[c] CV: coefficient of variation;
[d] Error rate = <averaged called percentage – molar percentage in sample>/molar percentage in sample.

TABLE 4

SVM scores of repeat measurements with same nanopore

| | Total Events | | | No. Features | SVM score | Molar percentage of CSdp20 in $HP_{dp20}$ | | | | |
|---|---|---|---|---|---|---|---|---|---|---|
| | | | | | | 1% | 5% | 10% | 20% | 50% |
| Nanopore | $HP_{dp20}$ | $CS_{dp20}$ | Mixtures | | | Percentage (%) of CSdp20 determined by SVM calling | | | | |
| Pore-1 | 399 | 914 | 631 | 7 | 98.3 | | | | | 46.1 |
| | | | | 10 | 97.4 | | | | | 45.1 |
| | | | | 11 | 98.0 | | | | | 44.8 |
| pore-1[a] | 278 | 195 | 957 | 10 | 100 | | | | | 57.2 |
| | | | | 11 | 100 | | | | | 62.3 |
| | | | | 12 | 99.6 | | | | | 65.3 |
| Pore-2 | 853 | 1012 | 1011/1933 | 6 | 91.9 | 1.2 | | 9.9 | | |
| | | | | 6 | 92.0 | 0.3 | | 12.4 | | |
| | | | | 11 | 93.3 | 1.4 | | 11.1 | | |
| Pore-3 | 219 | 845 | 2697/95 | 4 | 90.6 | 1.7 | 6.3 | | | |
| | | | | 4 | 90.6 | 2.0 | 8.7 | | | |
| | | | | 14 | 94.0 | 3.0 | 7.4 | | | |
| Pore-4 | 1731 | 1931 | 2180 | 9 | 82.5 | | | | 22.8 | |
| | | | | 14 | 84.0 | | | | 22.8 | |
| | | | | 15 | 84.1 | | | | 23.2 | |
| Pore-5 | 9663 | 1265 | 22029/9177 | 20 | 79.4 | 0.2 | 6.0 | | | |
| | | | | 23 | 83.3 | 0.5 | 3.9 | | | |
| | | | | 26 | 81.8 | 0.5 | 4.5 | | | |
| Pore-6 | 3317 | 1844 | 2560/2205 | 8 | 80.2 | | | 8.9 | 20.3 | |
| | | | | 10 | 80.8 | | | 9.3 | 21.9 | |
| | | | | 12 | 80.4 | | | 7.4 | 19.3 | |

Identification of unfractionated heparin and enoxaparin.

To explore its potential application in pharmaceutical production, the nanopore/SVM method was tested on samples with clinical uses, e.g. unfractionated heparin (UFH) and a LMWH (low molecular weight heparin) drug enoxaparin (enoxaparin sodium: CAS Reg. No. 9005-49-6, trade names: Lovenox®, Clexane®, Xaparin®). UFH and LMWH drugs are widely used in the prevention and treatment of thromboembolic disorders (Cosmi, B. et al, *Thromb. Res.* (2012) 129:388-91; Lee, S. et al, *Nat. Biotechnol.* (2013) 31:220-6). Enoxaparin, with an average MW of about 4500, is a product of depolymerizing the UFH, so called low molecular weight heparins (LMWH), a mixture of polydisperse oligosaccharides each containing an unsaturated urinate residue at its non-reducing end and an amino sugar or a 1,6-anhydro amino sugar at its reducing end. Nonetheless, the enoxaparin still remains about 20% of antithrombin-binding fractions of UFH (Mourier, P. A. et al, *J. Pharm. Biomed. Anal.* 2015, 115:431-42). Besides being shorter than UFH, enoxaparin is also polydisperse and contains an unsaturated uronate residue at its non-reducing end as well as an amino sugar or a 1,6-anhydro amino sugar at its reducing end, having the structure:

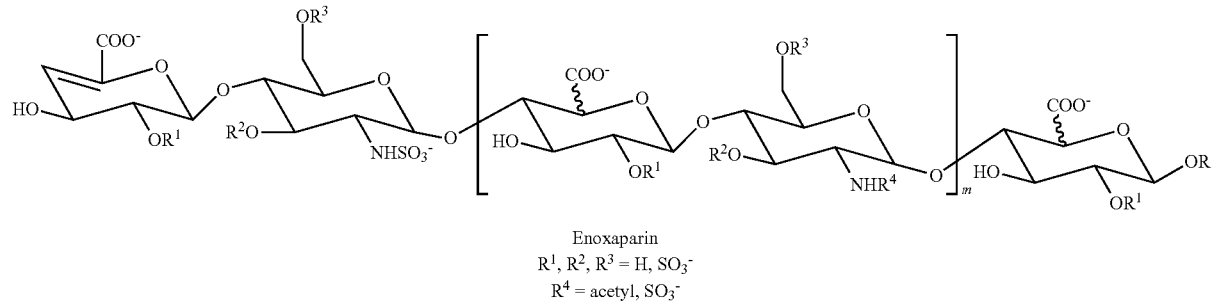

Enoxaparin
$R^1, R^2, R^3 = H, SO_3^-$
$R^4 = $ acetyl, $SO_3^-$

Figure 8A:
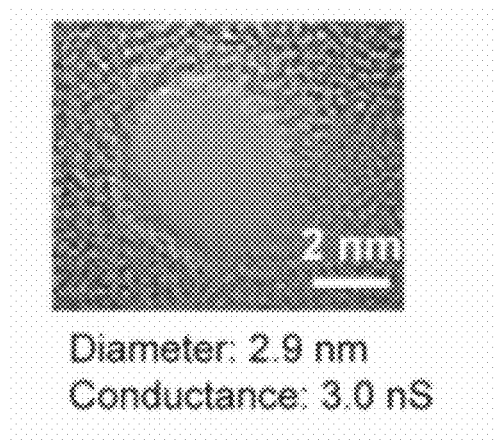
FIG. 8A shows TEM image of the nanopore used in the measurement.
Figure 8B:
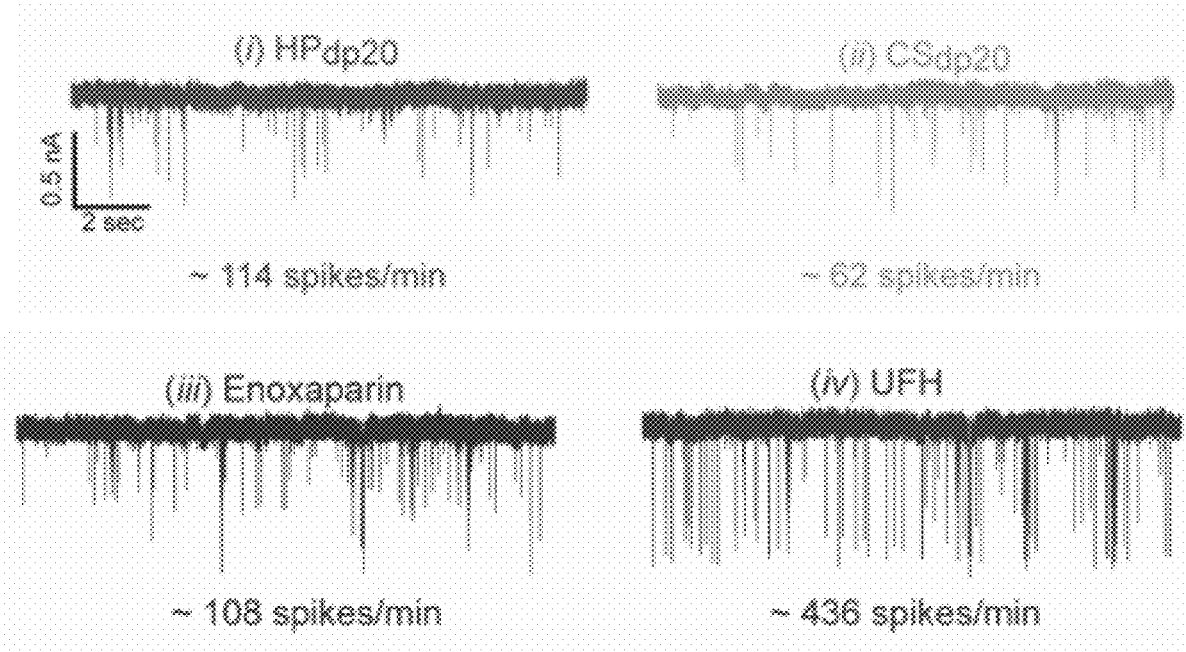
FIG. 8B shows typical ionic current traces of $HP_{dp20}$, and $CS_{dp20}$, enoxaparin, and UFH recorded under a voltage bias of 500 mV in 0.4 M KCl in phosphate buffer, pH 7.4.
Figure 8C:
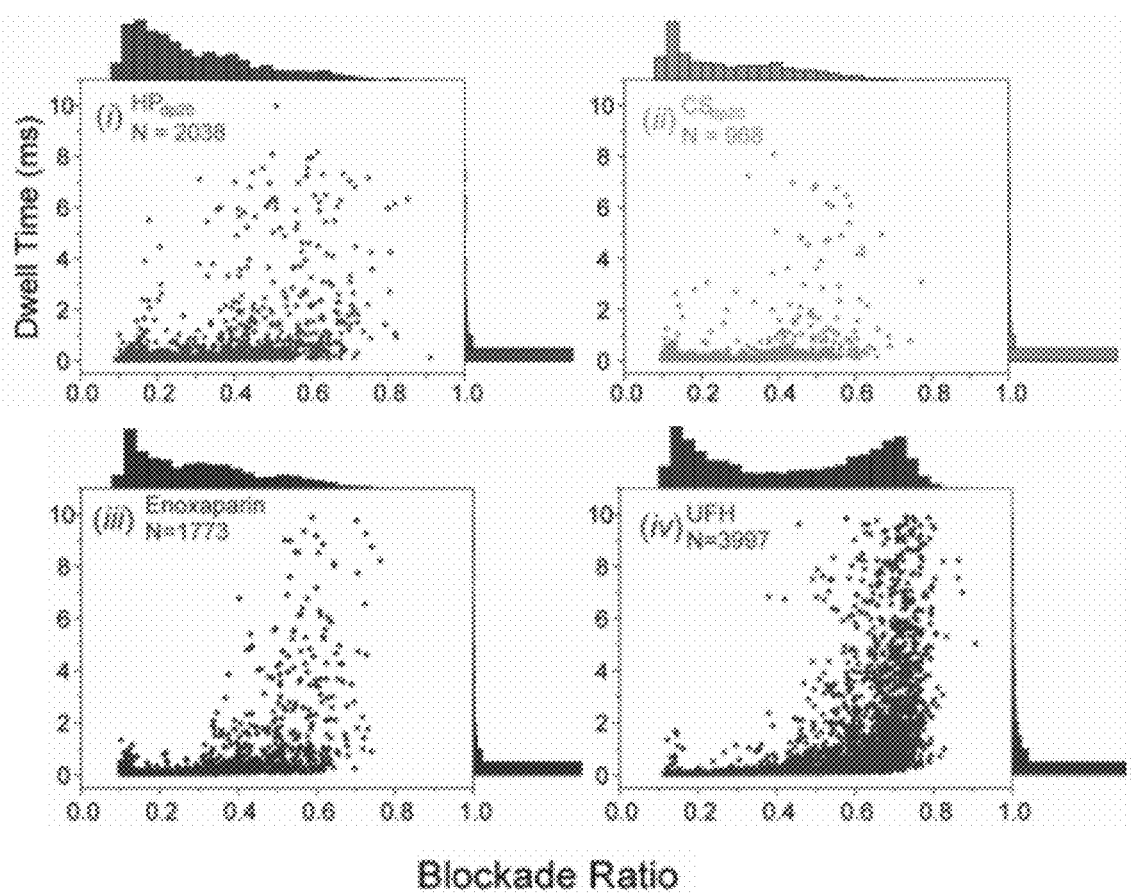
FIG. 8C shows scatter-plots of dwell time vs current blockade ratio of $HP_{dp20}$, and $CS_{dp20}$, enoxaparin, and UFH, accompanied with their respective marginal histograms.

Serial measurements of $HP_{dp20}$, $CS_{dp20}$, enoxaparin, and UFH were conducted at 1.0 μM concentrations using a newly drilled nanopore of about 3 nm in diameter (FIG. 8A). Between the measurements, there was a process of rinsing and baseline recovery. FIG. 8B displays the typical current traces of these GAG products recorded by the nanopore and their event rates which follow an order of UFH>$HP_{dp20}$>enoxaparin>$CS_{dp20}$. First, the current spikes of each product were characterized by their dwell times and blockade ratios, which were then placed in a 2D scatter plot (FIG. 8C). The most noticeable feature is that UFH displays a two-peaked distribution in its blockade ratios, one of which is located at the low end between 0.1 to 0.2, the same as the other GAGs, and the other located between 0.6 to 0.8, which can be attributed to a significant portion of high molecular weight fraction existing in UFH. Also, these GAG products have their dwell times in a range of 60 to 90 microseconds (μs) on average (Table 10). Since the data was recorded at a sampling rate of 500 kHz with 100 kHz low pass frequency bandwidth, the differences among those dwell times may not be significant.

TABLE 5

Dwell Times derived from curve fitting to the Lognormal function

|  | HPdp20 | CSdp20 | Enoxaparin | UFH |
| --- | --- | --- | --- | --- |
| Median (ms) | 0.063 | 0.074 | 0.064 | 0.061 |
| Mean (ms) | 0.069 | 0.091 | 0.071 | 0.083 |
| Adj. $R^2$ | 0.98 | 0.99 | 0.97 | 0.98 |

To identify these GAGs, 50% of the data was randomly selected from each of collected data sets to train the SVM with up to 88 available signal features and then applied the trained SVM to classify the rest of 50% remaining data. The effectiveness of SVM for the GAG identification is quickly determined without laborious multiple runs. The four products can be distinguished in pairs by SVM. All of SVMs were trained to be capable of identifying individual spikes in the training data with 100% accuracy, as a trained machine learning algorithm. As shown in Table 5, both UFH and $CS_{dp20}$ were called with an accuracy of 94.6% and 91.0%, respectively, 92.5% on average (Entry 1); UFH and enoxaparin (designated as Enox) with an accuracy of about 96% and 93%, respectively (Entry 2). However, UFH and $HP_{dp20}$ were distinguished with a lower accuracy of about 85% on average (Entry 3). For calling Enox, the SVM distinguished between Enox and $HP_{dp20}$ (Entry 5) marginally better than between UFH and $HP_{dp20}$. The SVM distinguished between Enox and $CS_{dp20}$ with an averaged accuracy of about 73% (Entry 4), significantly lower than it did between UFH and $CS_{dp20}$ which is consistent with the scatter plots in FIG. 8C, where the data points of $CS_{dp20}$ overlaps with those of enoxaparin more than those of UFH. SVM distinguished between $HP_{dp20}$ and $CS_{dp20}$ (Entry 6) better than between Enox and $CS_{dp20}$ (Entry 4), even though $HP_{dp20}$ has a molecular weight distribution overlapped with $CS_{dp20}$ more than enoxaparin does with $CS_{dp20}$ (FIG. 2A). Thus, the result may be better explained based on their Anion-Exchange (SAX)-HPLC chromatograms (FIG. 2B), where $HP_{dp20}$ has charged fragments overlapped with $CS_{dp20}$'S less than enoxaparin does. The nanopore shown in FIG. 5A had a higher accuracy for distinguishing between $HP_{dp20}$ and $CS_{dp20}$ than the one in FIG. 8A did. From their TEM images, these two nanopores had different shapes and diameters, which should contribute to the reduced accuracy. Furthermore, SVM was tested for calling all of the four GAG products from a pool of the nanopore data. The SVM called UFH with an accuracy of about 80% and the rest with accuracy around about 65% (Entry 7). These calling accuracies are statistically significant because the probability of a random pick would only be 25%. The better calling accuracy for UHF could be explained by the fact that UHF contains a portion of blockade currents well separated from those of the rest of the GAGs, which are overlapped with one another (FIG. 8C). Nonetheless, the low calling accuracy indicates that the data from a single nanopore would not be sufficient for SVM to call multiple GAGs all at once.

TABLE 6

Accuracy of SVM calling heparins and $CS_{dp20}$

| Entry | Entity | Training Accuracy (%) | Identification accuracy (%)[1] | | | | |
|---|---|---|---|---|---|---|---|
| | | | UFH | $CS_{dp20}$ | Enox. | $HP_{dp20}$ | Average |
| 1 | UFH vs $CS_{dp20}$ | 100 | 94.6 ± 1.2 | 91.0 ± 1.5 | | | 92.5 ± 1.0 |
| 2 | UFH vs Enox | 100 | 95.9 ± 0.9 | | 92.9 ± 0.9 | | 94.4 ± 0.6 |
| 3 | UFH vs $HP_{dp20}$ | 100 | 87.2 ± 1.6 | | | 82.1 ± 1.4 | 84.7 ± 1.1 |
| 4 | Enox vs $CS_{dp20}$ | 100 | | 73.8 ± 2.7 | 72.1 ± 1.7 | | 73.0 ± 1.6 |
| 5 | Enox vs $HP_{dp20}$ | 100 | | | 88.4 ± 2.3 | 86.4 ± 1.3 | 87.4 ± 1.3 |
| 6 | $HP_{dp20}$ vs $CS_{dp20}$ | 100 | | 88.7 ± 1.8 | | 83.3 ± 1.4 | 86.0 ± 1.1 |
| 7 | Pool of Four | 100 | 80.6 ± 1.6 | 65.1 ± 2.6 | 65.2 ± 3.3 | 64.8 ± 3.3 | 68.9 ± 1.4 |

[1]each value is an average of three calls by the SVMs trained from three randomly selected subsets of data.

Quantification of $HP_{dp20}$.

The use of solid-state nanopores was demonstrated for quantitation of sulfated GAGs. In the nanopore measurement, the event rate changes with the concentration of an analyte. Thus, the determination of concentrations becomes counting of spikes. Event rates linearly increased with concentrations of heparin in a range of 0.25 to 1.25 μM (a five-fold change). The $HP_{dp20}$ concentration was measured ranging from 1.0 nM to 100 μM using multiple nanopores to build a calibration curve with calibration samples. For the measurement, each concentration was repeated at least once in the same or a different nanopore. From the nanopore data was extracted all of the ionic current signals above a threshold as conducted for the SVM analysis, defining an event rate as spikes/s (Table 7). The event rate varied from nanopore to nanopore for the same concentration. That may be attributed to different diameters and shapes among these nanopores even though they were fabricated under the same TEM conditions.

TABLE 7

Translocation Frequencies of HPdp20 through nanopores (spikes/sec)

| Nanopore | | Sample dilution [μM] | | | | |
|---|---|---|---|---|---|---|
| pore | d [nm] | 0.001 | 0.01 | 0.05 | 0.1 | 0.5 |
| 1 | 3.3 | | | | 3.078 ± 0.529 | 3.259 ± 0.177 |
| 2 | 2.0 | 0.143 ± 0.014 | 0.199 ± 0.018 | 0.270 ± 0.057 | 0.358 ± 0.052 | |
| 2* | 2.0 | 0.147 ± 0.016 | | | 0.399 ± 0.041 | |
| 3 | 2.5 | | | | 0.760 ± 0.067 | |
| 4 | 2.5 | | 0.101 ± 0.011 | | 0.157 ± 0.015 | |
| 5 | 2.6 | 0.088 ± 0.012 | | 0.536 ± 0.158 | 0.859 ± 0.147 | 1.204 ± 0.109 |
| 6 | 3.2 | | | 0.272 ± 0.022 | 0.335 ± 0.047 | |
| 7 | 2.7 | 0.120 ± 0.017 | 0.138 ± 0.016 | | 0.441 ± 0.018 | |
| 8 | 3.6 | | 0.597 ± 0.053 | | 1.663 ± 0.510 | |

| Nanopore | | Sample dilution [μM] | | | |
|---|---|---|---|---|---|
| pore | d [nm] | 1 | 5 | 10 | 100 |
| 1 | 3.3 | 5.716 ± 0.299 | | | |
| 2 | 2.0 | | | 3.477 ± 0.211 | |
| 2* | 2.0 | | | | |
| 3 | 2.5 | 2.319 ± 0.656 | 3.503 ± 1.404 | | |
| 4 | 2.5 | | | | 6.891 ± 0.631 |
| 5 | 2.6 | | | 9.530 ± 0.947 | |
| 6 | 3.2 | 1.189 ± 0.207 | 2.098 ± 1.260 | | |
| 7 | 2.7 | 1.082 ± 0.080 | | | 9.573 ± 0.762 |
| 8 | 3.6 | 4.373 ± 0.507 | | | |

In order to compare the event rates between nanopores, all the event rates measured were normalized with the same nanopore by referencing the one at 0.1 μM as 1.0 (Table 8).

Figure 9A:
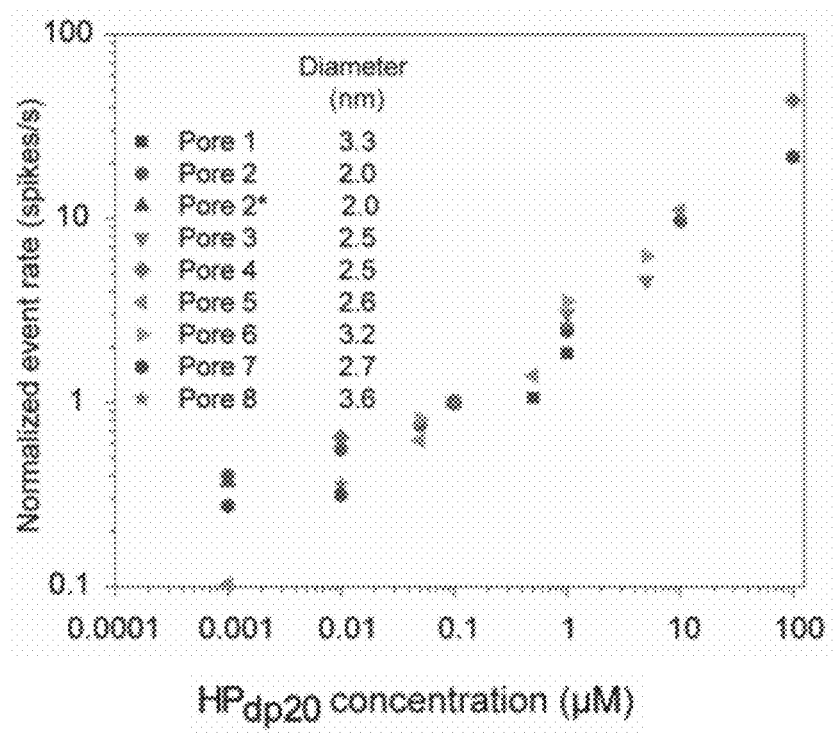
FIG. 9A shows a plot of spike frequency, event rates to the concentrations of $HP_{dp20}$ from individual nanopores.
Figure 9B:
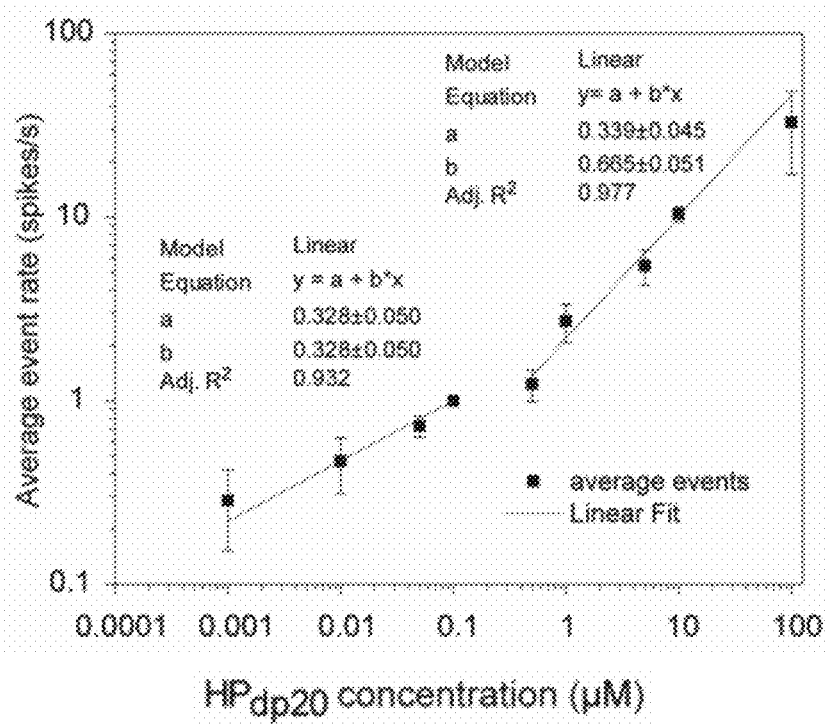
FIG. 9B shows a plot of averaged frequency event rates to the concentrations of $HP_{dp20}$ with their fitting lines. For the linear function, y=log (event rate) and x=log conc.

Pore 9), from which their concentrations were derived by applying either of the two functions in FIG. 9B, and then repeated the measurement with two of the samples using the

TABLE 8

Normalized frequencies (referenced to those from 0.1 μM sample as 1)

| Nanopore | | Sample dilution micromolar (μM) | | | | |
|---|---|---|---|---|---|---|
| pore | d [nm] | 0.001 | 0.01 | 0.05 | 0.1 | 0.5 |
| 1 | 3.3 | | | | 1.000 ± 0.172 | 1.058 ± 0.057 |
| 2 | 2.0 | 0.400 ± 0.041 | 0.554 ± 0.050 | 0.752 ± 0.160 | 1.000 ± 0.146 | |
| 2* | 2.0 | 0.368 ± 0.042 | | | 1.000 ± 0.103 | |
| 3 | 2.5 | | | | 1.000 ± 0.088 | |
| 4 | 2.5 | | 0.648 ± 0.070 | | 1.000 ± 0.099 | |
| 5 | 2.6 | 0.102 ± 0.014 | | 0.623 ± 0.184 | 1.000 ± 0.171 | 1.400 ± 0.127 |
| 6 | 3.2 | | | 0.812 ± 0.067 | 1.000 ± 0.141 | |
| 7 | 2.7 | 0.274 ± 0.039 | 0.314 ± 0.036 | | 1.000 ± 0.041 | |
| 8 | 3.6 | | 0.359 ± 0.032 | | 1.000 ± 0.306 | |
| Ave. | | 0.286 ± 0.133 | 0.469 ± 0.158 | 0.729 ± 0.096 | 1.000 ± 0.000 | 1.229 ± 0.241 |

| Nanopore | | Sample dilution micromolar (μM) | | | |
|---|---|---|---|---|---|
| pore | d [nm] | 1 | 5 | 10 | 100 |
| 1 | 3.3 | 1.856 ± 0.097 | | | |
| 2 | 2.0 | | | 9.688 ± 0.589 | |
| 2* | 2.0 | | | | |
| 3 | 2.5 | 3.051 ± 0.863 | 4.609 ± 1.847 | | |
| 4 | 2.5 | | | | 43.894 ± 4.024 |
| 5 | 2.6 | | | 11.085 ± 1.102 | |
| 6 | 3.2 | 3.551 ± 0.619 | 6.264 ± 3.762 | | |
| 7 | 2.7 | 2.453 ± 0.182 | | | 21.693 |
| 8 | 3.6 | 2.629 ± 0.305 | | | |
| Ave. | | 2.708 ± 0.637 | 5.436 ± 1.170 | 10.386 ± 0.987 | 32.793 ± 15.69 |

The normalized data plotted on a log-log scale (FIG. 9A) appear to increase exponentially with concentrations of $HP_{dp20}$. However, their averages in the low and high concentration regions can separately be fit into two different linear functions of the logarithmic variables, as displayed in FIG. 9B which is consistent with changes of event rates with the DNA concentrations. The data also indicates that the event rates change more rapidly in the micromolar (μM) region than in the nanomolar (nM) region. It is estimated that the nanopore measurement for the detection of $HP_{dp20}$ can reach a nanomolar (nM) level with a 5-Log dynamic range, a standard curve for the determination of $HP_{dp20}$ concentrations.

Using two newly fabricated nanopores, the standard curve was tested for the $HP_{dp20}$ samples. In the same way as shown in FIGS. 9A and 9B, the 0.1 μM $HP_{dp20}$ sample was used as a control and its event rates in the nanopores were referenced as 1.0 (Table 7).

second nanopore (designated as Pore 10). The results show that each concentration determined by the single nanopores considerably deviates from its actual value in the tested sample and also varies from nanopore to nanopore. For example, the 0.01 μM sample was determined as 0.008 μM by Pore 9 and 0.013 μM by Pore 10. However, the average of these two measurements is 0.011, only 10% off from the actual concentration. For the 1.0 μM sample, the average of measurements by these two nanopores is 0.9 M, just 10% lower than expected. At the higher 5.0 μM concentration, the concentration determined by a single nanopore measurement deviated from the actual value by 6%, demonstrating that the nanopore can be used to quantify the sulfated GAG samples by introducing a reference sample for the nanopore calibration. Moreover, the multiple-nanopore measurement may achieve a high accuracy when the sample concentration is below micromolar (μM) level.

TABLE 9

Raw and normalized event rate of the pores used in Table 10

| Pore | | Concentration [μM] | | | | |
|---|---|---|---|---|---|---|
| Index | | 0.01 | 0.05 | 0.1 | 1 | 5 |
| 5-1 | Raw Event Rate | 0.676 | 1.002 | 1.573 | 2.396 | 9.714 |
| | Normalized Event Rate | 0.430 | 0.637 | 1.000 | 1.523 | 6.175 |
| | Determined conc. | 0.008 | 0.03 | — | 0.6 | 4.7 |
| 5-2 | Raw Event Rate | 0.796 | — | 1.563 | 3.854 | — |
| | Normalized Event Rate | 0.509 | — | 1.000 | 2.466 | — |
| | Determined conc. | 0.013 | — | — | 1.2 | — |

As shown in Table 10, four $HP_{dp20}$ samples were measured for their event rates with a nanopore (designated as

TABLE 10

Fitting functions for determination of $HP_{dp20}$ concentration by nanopores

| | | Concentration Measurement | | | |
|---|---|---|---|---|---|
| Pore | Sample conc. (μM) | 0.01 | 0.05 | 1.0 | 5.0 |
| 9 | Event rate* (spikes/s) | 0.430 | 0.637 | 1.523 | 6.175 |
| | Derived conc. (μM) | 0.008 | 0.025 | 0.6 | 4.8 |
| 10 | Event rate* (spikes/s) | 0.509 | — | 2.466 | — |
| | Derived conc. (μM) | 0.013 | — | 1.20 | — |
| | Average (μM) | 0.011 ± 0.004 | | 0.90 ± 0.42 | |

*normalized event rates and see Table 7 for their raw data.

A nanopore/SVM method for identification of sulfated GAGs is demonstrated that distinguishes between heparins as well as between heparin and chondroitin sulfate with high accuracies. The nanopore/SVM method was also able to identify $CS_{dp20}$ in its mixtures with $HP_{dp20}$ at a level down to 0.8% (w/w), comparable to the NMR technique for detection of OSCS. Besides its bulkiness and expensiveness, NMR spectrometers also require more materials for the analysis.

To address the issue on non-uniformity of nanopore size and geometry, a reference sample (calibration sample) was used for the calibration of nanopores (0.1 µM $HP_{dp20}$) which allowed normalization of the data from different nanopores. It was observed $HP_{dp20}$ can be quantified with reasonable accuracy by the multiple-nanopore measurement. Nanopore measurement has a nanomolar (nM) limit of detection and five orders of magnitude dynamic range. Thus, such a nanopore device can potentially be used to monitor the heparin level in the human blood since the range of plasma heparin is about 1 to 2.4 mg per liter, equivalent to a range of 67 to 160 nM (assuming an average molecular weight of 15,000 for UFH). An array of nanopores may be produced and used to optimize different machine learning algorithms for the identification of GAGs.

EXAMPLES

Example 1 Fabrication of Nanopores

Silicon chips (5×5 mm) coated with silicon nitride (30 nm thick) were purchased from Norcada Inc. (part number: NX5025X). Following a process of argon plasma cleaning, nanopores were drilled using the electron beam in JEOL 2010FEG and ARM 200F transmission electron microscope (TEM) at 200 keV. The size of the pores was controlled by the electron beam size and exposure time. The nanopores were imaged right after the drilling. The nanopore was drilled in a 30 nm-thick silicon nitride membrane by TEM, which shows a conical shape with a diameter of about 3.2 nm at its narrowest section (FIG. 8A).

Example 2 Preparation of Sample Solutions

Stock solutions of $HP_{dp20}$ and $CS_{dp20}$ (Iduron) were prepared respectively by dissolving the sample in $H_2O$. Their actual concentrations were determined based on the carbazole assays. These two stock solutions of $HP_{dp20}$ (10 mM) and $CS_{dp20}$ (10 mM) were used to prepare mixtures of $HP_{dp20}$ and $CS_{dp20}$ with a ratio of 1, 5, 10, 20, and 50% of $CS_{dp20}$. The final concentrations of these mixtures were diluted to be 0.5-1 µM with an electrolyte solution of 0.4 M KCl in 1 mM phosphate buffer (pH 7.4). For the dilution study, the 10 mM stock solution of $HP_{dp20}$ was diluted to various concentrations in a range of 1 mM to 10 nM and injected into the cis reservoir to make the final concentrations of the analyte 100 µM to 1 nM for the measurement.

Example 3 Nanopore Measurements

Prior to the measurement, a nanopore chip was cleaned by immersing in a hot piranha acid (piranha etch) solution ($H_2O_2$:$H_2SO_4$=1:4) for 20 min, and then rinsed with Milli-Q water (a resistivity of about 18.2 MΩ×cm and total organic carbon of less than 5 ppb). Piranha acid solutions are extremely energetic and may result in explosion or skin burns if not handled with extreme caution. After drying with $N_2$ gas, the nanopore chip was placed in a piranha-cleaned PCTFE cell to form a cis reservoir and sealed with a quick-curing silicone elastomer gasket. The PCTFE cell with a nanopore chip was then assembled with a PTFE base to form a trans reservoir. The electrolyte solution used was 0.4 M KCl in 1 mM phosphate buffer (pH 7.4), which was filtered with a Millipore 0.2 µm filter. Ag/AgCl electrodes, freshly made from Ag wires with bleach, were inserted into both cis and trans reservoirs for ionic current measurement. All of analytes were dissolved in the electrolyte solution for the nanopore analysis.

For the measurement, both cis and trans reservoir were filled with the electrolyte solution, and the nanopore was soaked for about 1 to 2 hours, followed by applying a high voltage (about 1 V) between two reservoirs for about 5 to 10 minutes to obtain a steady baseline current and no electrical spikes, an indicator of achieving an open and wet nanopore. Then, an analyte solution (about 10 µl) was injected into the cis reservoir with a final concentration of about 1 µM. A translocation bias was applied to the Ag/AgCl electrode in the trans reservoir, while the electrode in the cis reservoir was kept grounded to avoid adsorption of analyte molecules to the reference electrode. After recording the ionic current, the cis reservoir was drained and rinsed with the electrolyte solution. Another baseline was recorded to ensure no contaminations left in cis reservoir before a new analyte solution was injected.

TABLE 11

SVM scores of repeat measurements with same nanopore

| | SVM Training | | | | SVM score on trained data set | | SVM score on untrained data set | |
|---|---|---|---|---|---|---|---|---|
| SVM Index | Training Data (Prediction Data) | No. Features | Training Score | Analyte (Events) | $HP_{dp20}$ (609) | $CS_{dp20}$ (361) | $HP_{dp20}$ (1640) | $CS_{dp20}$ (1271) |
| SVM-1 | Run-1 (Run-2) | 11 | 100 | $HP_{dp20}$ (610) | 92.6 | 9.4 | 93.4 | 6.5 |
| | | | | $CS_{dp20}$ (361) | 7.4 | 90.6 | 6.6 | 93.5 |
| SVM-2 | Run-1 (Run-2) | 11 | 100 | $HP_{dp20}$ (610) | 93.2 | 7.9 | 94.2 | 4.9 |
| | | | | $CS_{dp20}$ (361) | 6.8 | 92.1 | 5.8 | 95.1 |
| SVM-3 | Run-1 (Run-2) | 9 | 100 | $HP_{dp20}$ (610) | 93.4 | 12.4 | 95.6 | 7.1 |
| | | | | $CS_{dp20}$ (361) | 6.6 | 87.6 | 4.4 | 92.9 |

TABLE 11-continued

SVM scores of repeat measurements with same nanopore

| | SVM Training | | | | SVM score on trained data set | | SVM score on untrained data set | |
|---|---|---|---|---|---|---|---|---|
| SVM Index | Training Data (Prediction Data) | No. Features | Training Score | Analyte (Events) | $HP_{dp20}$ (820) | $CS_{dp20}$ (636) | $HP_{dp20}$ (1219) | $CS_{dp20}$ (722) |
| SVM-4 | Run-2 (Run-1) | 11 | 100 | $HP_{dp20}$ (820) | 96.2 | 6.0 | 93.7 | 8.8 |
| | | | | $CS_{dp20}$ (635) | 3.8 | 94.0 | 6.3 | 91.2 |
| SVM-5 | Run-2 (Run-1) | 10 | 100 | $HP_{dp20}$ (820) | 95.0 | 6.0 | 88.1 | 5.8 |
| | | | | $CS_{dp20}$ (635) | 5.0 | 94.0 | 11.9 | 94.2 |
| SVM-6 | Run-2 (Run-1) | 8 | 100 | $HP_{dp20}$ (820) | 95.8 | 8.8 | 91.2 | 7.6 |
| | | | | $CS_{dp20}$ (635) | 4.2 | 91.2 | 8.8 | 92.4 |

Example 4 Data Collection

Ionic currents were collected at a 500 kHz sampling rate with a 100 kHz low pass filter using patch clamp amplifier Axon Axopatch 200B, with digitizer DigiData 1550A from Axon Instruments Inc. PClamp 10.4 software and an in-house developed LabView program were used for data recording.

Example 5 SVM Data Analysis

A program written in MATLAB was used for the data process to identify GAGs. First, a baseline of recorded ionic currents was determined by the most probable electrical current, the width of which was determined by 6σ (standard deviation) of the trace. Those spikes larger than the baseline width were recognized as translocation events. Then, each of them was subjected to Fourier transformation by down-sampling it to 20 equal frequency bins, corresponding to 25 kHz bin size. The Fourier transformed frequency spectrum was further transformed to cepstrum domain and down-sampled into 51 equal bins (FIG. 6). As a result, a total of 88 signal features were created from the three domains (Table 12).

TABLE 12

Features and their descriptions for SVM data analysis

| Feature Name | Description |
|---|---|
| Amplitude | Maximum amplitude of the event. |
| Average Amplitude | Average amplitude of the event. |
| Dwell Time | Width of the event. |
| Blockade Ratio | Ratio of the maximum amplitude of the event with respect to the baseline. |
| Number of Levels | Number of levels of the event. |
| Step Size | Magnitude of the differences between levels. (Zero was assigned for no leveled event.) |
| Fluctuation | Number of local maximum peaks of the event. |
| Roughness | Standard deviation of the event. |
| Peak in Beginning | Maximum amplitude of the first 10 μs data of the event. (First a-third data for the event shorter than 30 μs.) |
| Peak in Middle | Maximum amplitude of the data out of the first and last 10 μs of the event. (Second a-third data for the event shorter than 30 μs.) |
| Peak in Last | Maximum amplitude of the last 10 μs data of the event. (Last a-third data for the event shorter than 30 μs.) |
| Peak FFT 1-20 | The normalized power spectrum, down-sampled into 20 equal frequency bands. |
| Peak FFT Total | Total summation of frequency spectra of the event. |
| Peak FFT Maximum 1-4 | The 'n-th' dominant frequency band on the power spectrum. |
| Peak HighLow | The ratio of the top quarter of the power spectrum to bottom quarter of the spectrum. |
| Peak Cepstrum 1-51 | Average magnitude of the cepstrum spectra down-sampled into 51 equal windows of the event. |

To avoid features with a large numeric range from dominating those with a small numeric range, all the calculated features were normalized to make the mean of each feature with its standard deviation between 0 and 1. The normalized correlation was calculated between different pairs of all the features and selected one of them as a representative feature for the following analysis. The features were ranked according to the ratio between the in-group fluctuation (variation over repeated experiments of the same analyte) and the out-group fluctuation (variation between different analytes), and then the low ranked features were removed. Those survived features were evaluated by the classification accuracy, from which an optimized set of features was chosen to achieve a maximum true positive accuracy. The SVM was run with the kernel-mode adapted from https://github.com/vjethava/svm-thetai and its running parameters C and gamma were optimized through cross-validation of randomly selected sub-data set.

Statistical analysis was carried out in OriginPro 2017, in which the Levenberg-Marquardt algorithm was used for the curve fitting.

Computational Modeling, DFT calculations were performed using Spartan'16 for Windows, available software from Wave Function, Inc. Two dimensional molecular structures were drawn in ChemDraw Ultra 12.0 and imported to Spartan'16 to generate corresponding 3D structures. Each structure was subjected to energy minimization using the built-in MMFF molecular mechanics prior to optimization calculation. The DFT calculations were performed at their ground-state equilibrium geometry conformation using B3LYP/6-31G* basis set in vacuum.

Although the foregoing invention has been described in some detail by way of illustration and example for purposes of clarity of understanding, the descriptions and examples should not be construed as limiting the scope of the invention. Accordingly, all suitable modifications and equivalents may be considered to fall within the scope of the invention as defined by the claims that follow. The disclosures of all patent and scientific literature cited herein are expressly incorporated in their entirety by reference.

What is claimed is:

1. A method for characterizing the purity of glycosaminoglycans, comprising:
    (a) passing one or more calibration samples through a first silicon nitride nanopore while recording a translocation current signal;
    (b) passing a negatively charged glycosaminoglycan sample to be characterized through the first silicon nitride nanopore or a second silicon nitride nanopore while recording a translocation current signal; and
    (c) using a machine learning algorithm to determine the purity of the negatively charged glycosaminoglycan sample to be characterized from the translocation current signals;
    wherein the negatively charged glycosaminoglycan molecule translocates through a silicon nitride nanopore under a voltage bias and wherein the voltage bias causes a transient blockade of ionic current and generates a current spike.

2. The method of claim 1 wherein the machine learning algorithm extracts data by Fourier transform (FFT) and cepstrum transform of the nanopore data recorded in the time domain to index individual current spikes.

3. The method of claim 1 wherein the negatively charged glycosaminoglycan sample is passed through more than one nanopore.

4. The method of claim 2 wherein the nanopore data is a sum of molecular bumping and translocating events.

5. The method of claim 3, wherein the more than one nanopore have different shapes.

6. The method of claim 3, wherein the more than one nanopore have different sizes.

* * * * *